US010894128B2

(12) United States Patent
Bokelman et al.

(10) Patent No.: US 10,894,128 B2
(45) Date of Patent: Jan. 19, 2021

(54) DRIVE CONTROL MECHANISMS AND AUTOMATIC INJECTORS FOR INJECTABLE CARTRIDGES

(71) Applicant: UNL Holdings LLC, New York, NY (US)

(72) Inventors: Kevin Bokelman, San Diego, CA (US); George M. Wohlhieter, Escondido, CA (US); Thomas F. McGee, San Diego, CA (US); Arthur G. Marlin, Willow Grove, PA (US); Stefanie A. Hurowitz, Fort Washington, PA (US); David R. Jansen, Glenmoore, PA (US); Ellen Ni Chathail, Castlebar (IE)

(73) Assignee: UNL HOLDINGS LLC, New York, NY (US)

( * ) Notice: Subject to any disclaimer, the term of this patent is extended or adjusted under 35 U.S.C. 154(b) by 70 days.

(21) Appl. No.: 16/031,419

(22) Filed: Jul. 10, 2018

(65) Prior Publication Data
US 2019/0038837 A1    Feb. 7, 2019

Related U.S. Application Data

(63) Continuation of application No. 14/572,161, filed on Dec. 16, 2014, now Pat. No. 10,046,115, which is a
(Continued)

(51) Int. Cl.
*A61M 5/20*    (2006.01)
*A61M 5/24*    (2006.01)
*A61M 5/315*   (2006.01)

(52) U.S. Cl.
CPC ............ *A61M 5/2033* (2013.01); *A61M 5/20* (2013.01); *A61M 5/24* (2013.01);
(Continued)

(58) Field of Classification Search
CPC ..................... A61M 2005/206; A61M 5/20
See application file for complete search history.

(56) References Cited

U.S. PATENT DOCUMENTS 3,395,704 A    8/1968    Frey et al.
D252,823 S     9/1979    Withers et al.
(Continued)

FOREIGN PATENT DOCUMENTS

AU    2003275893 B2    6/2004
CN    100553700 C      10/2009
(Continued)

OTHER PUBLICATIONS

Notice of Allowance, U.S. Appl. No. 14/572,161, entitled "Drive Control Mechanisms and Automatic Injectors for Injectable Cartridges." dated Apr. 10, 2018.
(Continued)

*Primary Examiner* — Laura A Bouchelle
(74) *Attorney, Agent, or Firm* — Hamilton, Brook, Smith & Reynolds, P.C.

(57) ABSTRACT

An automatic injector includes a housing having a guide, a drive control mechanism, a transmission assembly, a motor, and an energy source. The housing may further include a cartridge cover. A drive control mechanism includes a drive screw, a cartridge carrier, a plunger carrier, and one or more control transfer instruments, such as a puck or cylinder. The drive screw interfaces and connects with the plunger carrier. The automatic injector is configured to accept a variety of syringes as cartridges for drug delivery. The cartridges may be ejected from the injector and safely disposed after use, making the injector a reusable automatic injector. The reusable automatic injector may further include one or more sensors, such as a cartridge sensor and a patient sensor. The novel incorporation of the drive control mechanisms into the automatic injectors of the present invention enables a single
(Continued)

motor and transmission assembly to drive the function of multiple components, which may include the steps of: preparation and alignment of a cartridge for injection, removal of a safety cap or needle shield, needle injection, drug dose delivery, and syringe and/or needle retraction. Methods of manufacture and methods of use are also disclosed.

17 Claims, 17 Drawing Sheets

Related U.S. Application Data continuation of application No. 13/934,958, filed on Jul. 3, 2013, now Pat. No. 8,920,374.

(60) Provisional application No. 61/683,499, filed on Aug. 15, 2012, provisional application No. 61/668,303, filed on Jul. 5, 2012.

(52) U.S. Cl.
CPC .... *A61M 5/31513* (2013.01); *A61M 5/31515* (2013.01); *A61M 5/31581* (2013.01); *A61M 2205/502* (2013.01)

(56) References Cited

U.S. PATENT DOCUMENTS

| | | | |
|---|---|---|---|
| D262,319 S | 12/1981 | Kenney | |
| 5,425,715 A | 6/1995 | Dailing et al. | |
| D368,961 S | 4/1996 | Himbert et al. | |
| 6,083,199 A | 7/2000 | Thorley et al. | |
| 6,090,070 A | 7/2000 | Hager et al. | |
| 6,270,479 B1 * | 8/2001 | Bergens | A61M 5/2033 604/156 |
| D450,843 S | 11/2001 | McGuckin et al. | |
| D453,569 S | 2/2002 | Himbert | |
| 6,387,078 B1 | 5/2002 | Gillespie, III | |
| D476,734 S | 7/2003 | Pavlu et al. | |
| 6,585,698 B1 | 7/2003 | Packman et al. | |
| 6,607,508 B2 | 8/2003 | Knauer | |
| 6,830,551 B1 | 12/2004 | Uchigaki et al. | |
| 7,381,201 B2 | 6/2008 | Gilbert et al. | |
| 7,500,967 B2 | 3/2009 | Thorley et al. | |
| 7,736,353 B2 | 6/2010 | Reynolds | |
| 7,744,582 B2 | 6/2010 | Sadowski et al. | |
| 7,935,087 B2 | 5/2011 | Judd et al. | |
| 8,002,745 B2 | 8/2011 | Kaal et al. | |
| 8,021,333 B2 | 9/2011 | Kaal et al. | |
| 8,052,654 B2 | 11/2011 | Kaal et al. | |
| 8,114,050 B2 | 2/2012 | Kaal et al. | |
| D660,420 S | 5/2012 | Shaw et al. | |
| 8,167,937 B2 | 5/2012 | Cerruti et al. | |
| 8,366,669 B2 | 2/2013 | Donald et al. | |
| D677,785 S | 3/2013 | Stones et al. | |
| 8,702,653 B2 | 4/2014 | Samandi et al. | |
| 8,808,244 B2 | 8/2014 | Adlon et al. | |
| 8,920,374 B2 | 12/2014 | Bokelman et al. | |
| D764,657 S | 8/2016 | Bokelman et al. | |
| 10,046,115 B2 | 8/2018 | Bokelman | |
| 2001/0037087 A1 | 11/2001 | Knauer | |
| 2005/0080377 A1 | 4/2005 | Sadowski et al. | |
| 2005/0277886 A1 | 12/2005 | Hommann et al. | |
| 2006/0184137 A1 | 8/2006 | Reynolds | |
| 2006/0258990 A1 | 11/2006 | Weber | |
| 2007/0197968 A1 | 8/2007 | Pongpairochana et al. | |
| 2009/0254048 A1 | 10/2009 | Hetherington | |
| 2010/0042129 A1 | 2/2010 | Curry | |
| 2011/0015572 A1 | 1/2011 | Thorley et al. | |
| 2011/0092954 A1 | 4/2011 | Jennings | |
| 2011/0224622 A1 | 9/2011 | Karlsson | |
| 2012/0056019 A1 | 3/2012 | Renz et al. | |
| 2014/0012229 A1 | 1/2014 | Bokelman | |
| 2014/0018775 A1 | 1/2014 | Swords et al. | |
| 2015/0045729 A1 | 2/2015 | Denzer | |
| 2015/0174326 A1 | 6/2015 | Bokelman | |

FOREIGN PATENT DOCUMENTS

| | | |
|---|---|---|
| CN | 101730558 A | 6/2010 |
| DE | 20 2009 003009 U1 | 6/2009 |
| EP | 2331171 | 6/2011 |
| FR | 1538565 A | 9/1968 |
| GB | 2461732 A | 1/2010 |
| JP | 2007-500561 A | 1/2007 |
| JP | 2007-504867 A | 3/2007 |
| JP | 2008-543500 A | 12/2008 |
| JP | 2011 516153 A | 5/2011 |
| JP | 2015-521920 A | 8/2015 |
| SU | 55498 A1 | 11/1938 |
| WO | WO 1994/21316 A1 | 9/1994 |
| WO | WO 1995/004562 A1 | 2/1995 |
| WO | WO 03/008023 A1 | 1/2003 |
| WO | WO 2004/000395 A1 | 12/2003 |
| WO | WO 2004/047890 A1 | 6/2004 |
| WO | WO 2004/047891 A1 | 6/2004 |
| WO | WO 2005/018721 A1 | 3/2005 |
| WO | WO 2006/108243 A2 | 10/2006 |
| WO | WO 2006/119570 A1 | 11/2006 |
| WO | WO 2007/002052 A2 | 1/2007 |
| WO | WO 2007/036676 A1 | 4/2007 |
| WO | WO 2009/003234 A1 | 1/2009 |
| WO | WO 2009/007229 A1 | 1/2009 |
| WO | WO 2009/063030 A1 | 5/2009 |
| WO | WO 2009/153540 A1 | 12/2009 |
| WO | WO 2009/153543 A1 | 12/2009 |
| WO | WO 2010/049239 A1 | 5/2010 |
| WO | WO 2010/099850 A1 | 9/2010 |
| WO | WO 2011/057335 A1 | 5/2011 |
| WO | WO 2011/075760 A1 | 6/2011 |
| WO | WO 2013/028906 A1 | 6/2011 |
| WO | WO 2011/089417 A1 | 7/2011 |
| WO | WO 2011/109205 A1 | 9/2011 |
| WO | WO 2011/137488 A1 | 11/2011 |
| WO | WO 2011/141907 A1 | 11/2011 |
| WO | WO 2012/098371 A1 | 7/2012 |
| WO | 2014/008393 A1 | 1/2019 |

OTHER PUBLICATIONS

International Search Report, International Application No. PCT/US2013/049314, entitled: "Drive Control Mechanisms and Automatic Injectors for Injectable Syringes," dated Oct. 15, 2013.

Written Opinion, International Application No. PCT/US2013/049314, entitled: "Drive Control Mechanisms and Automatic Injectors for Injectable Syringes," dated Oct. 15, 2013.

International Preliminary Report on Patentability, International Application No. PCT/US2013/049314, entitled: "Drive Control Mechanisms and Automatic Injectors for Injectable Syringes," dated Jan. 6, 2015.

Extended European Search Report, EP Application No. 16153882.2, dated Jul. 18, 2016.

Office Action, U.S. Appl. No. 14/572,161, dated Feb. 7, 2018.

Non-Final Office Action, U.S. Appl. No. 14/572,161, dated Jun. 29, 2017.

Notice of Allowance, U.S. Appl. No. 13/934,958, dated Sep. 26, 2014.

Non-Final Office Action, U.S. Appl. No. 13/934,958, dated Jun. 9, 2014.

Non-Final Office Action, U.S. Appl. No. 29/459,890, dated Oct. 23, 2015.

Notice of Allowance, U.S. Appl. No. 29/459,890, dated Apr. 13, 2016.

Unilife, Lisa Auto-Injector, Aug. 4, 2013, http://www.unilife.com/product-platforms/auto-injectors/lisa-auto-injector.

International Search Report, International Application No. PCT/US2012/052129, entitled: Auto-Injector for Retractable Prefilled Syringe, dated Dec. 11, 2012.

(56) References Cited

OTHER PUBLICATIONS

International Search Report, International Application No. PCT/US2013/024819, entitled: "Plunger Sub-Assemblies and Auto-Injectors Having Low Retraction Activation Force," dated Apr. 16, 2013.
Written Opinion, International Application No. PCT/US2012/052129, entitled: "Auto-Injector for Retractable Prefilled Syringe," dated Dec. 11, 2012.
Written Opinion, International Application No. PCT/US2013/024819, entitled: "Plunger Sub-Assemblies and Auto-Injectors Having Low Retraction Activation Force," dated Apr. 16, 2013.
International Preliminary Report on Patentability, International Application No. PCT/US2013/024819, entitled: "Plunger Sub-Assemblies and Auto-Injectors Having Low Retraction Activation Force," dated Aug. 21, 2014.
International Search Report and Written Opinion, International Application No. PCT/US2014/034974, entitled: "Plunger-Driven Auto-Injectors," dated Jul. 28, 2014.

* cited by examiner

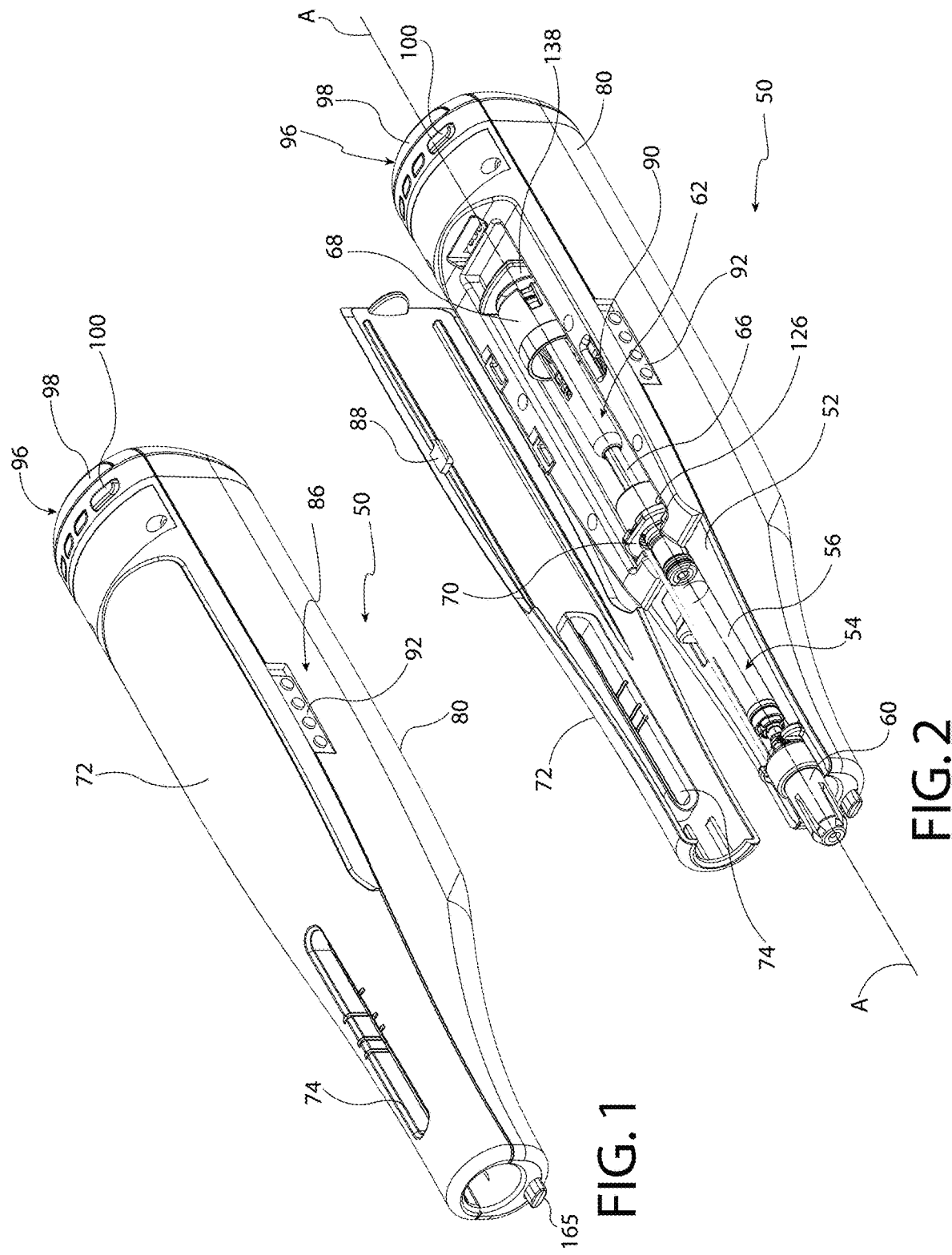

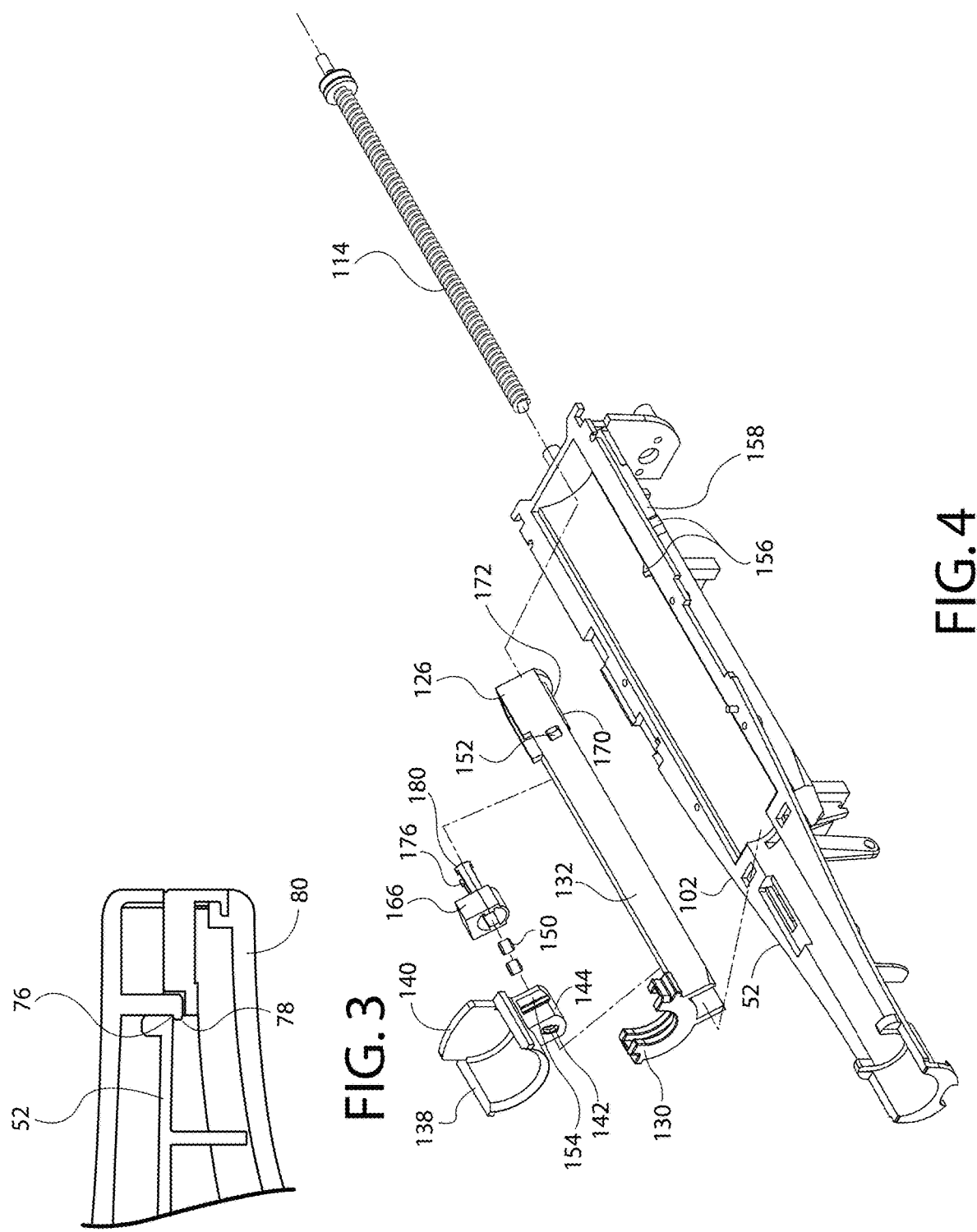

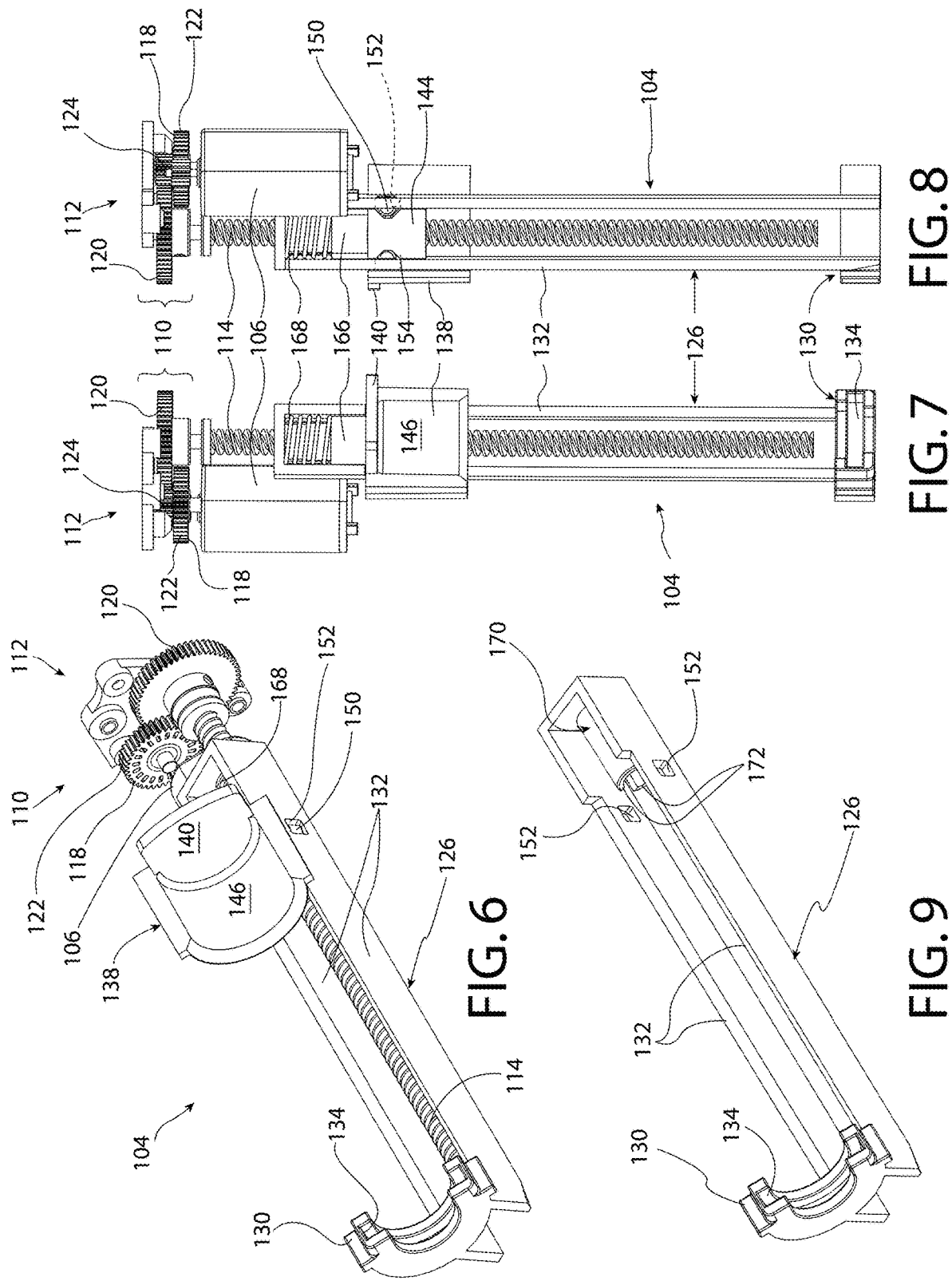

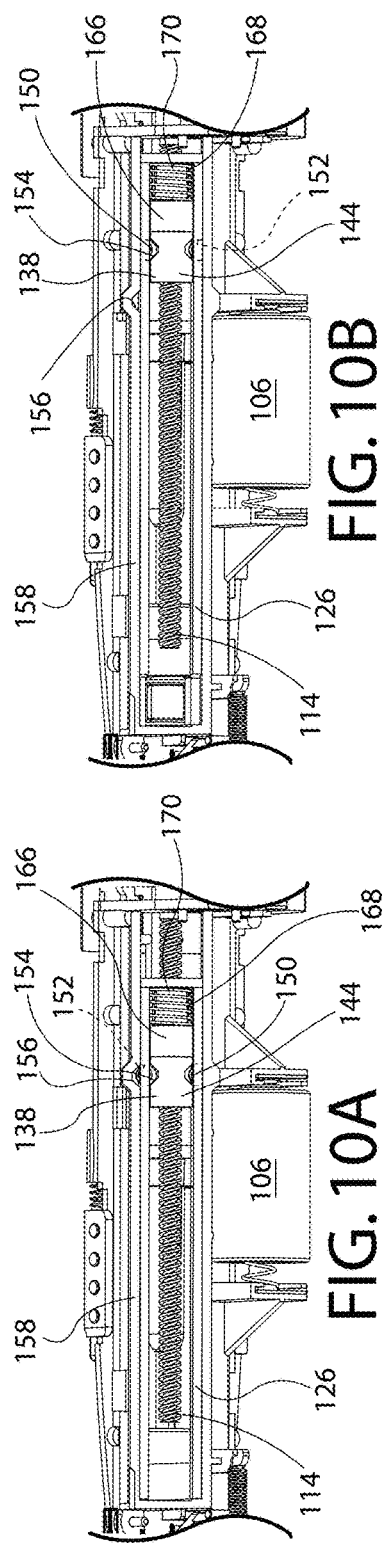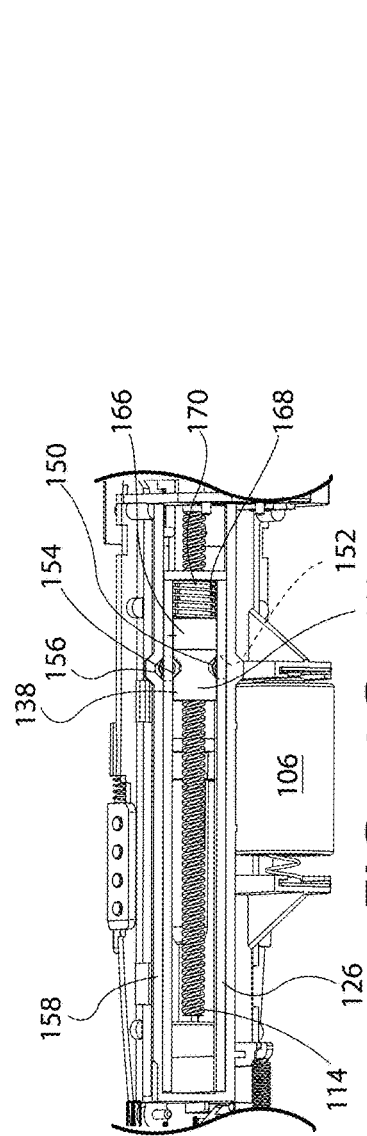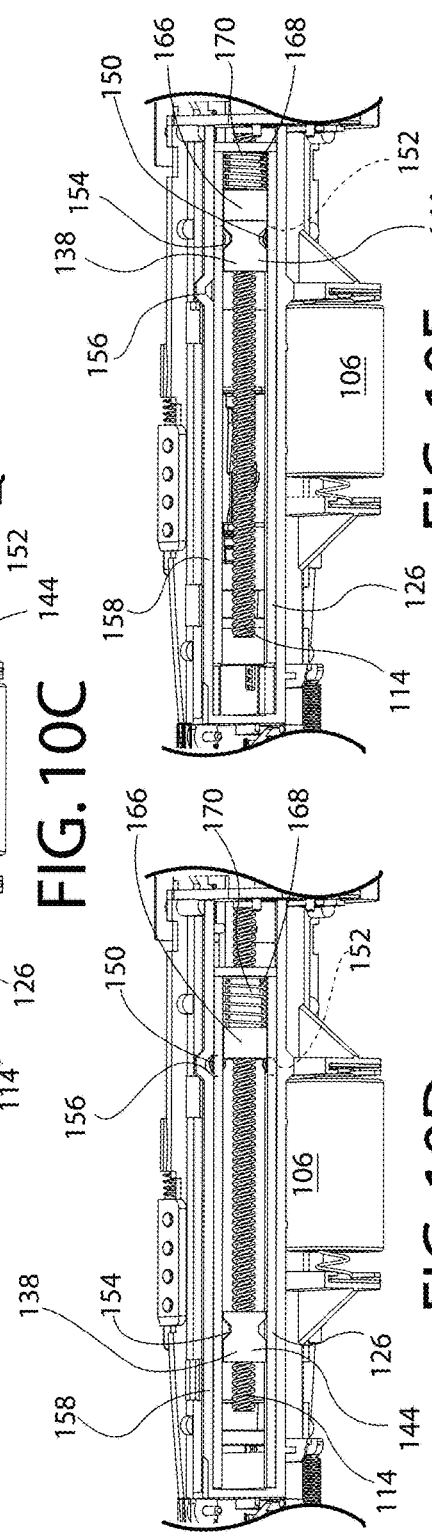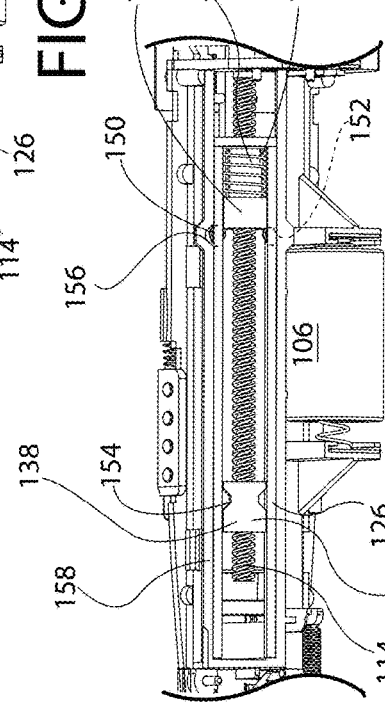

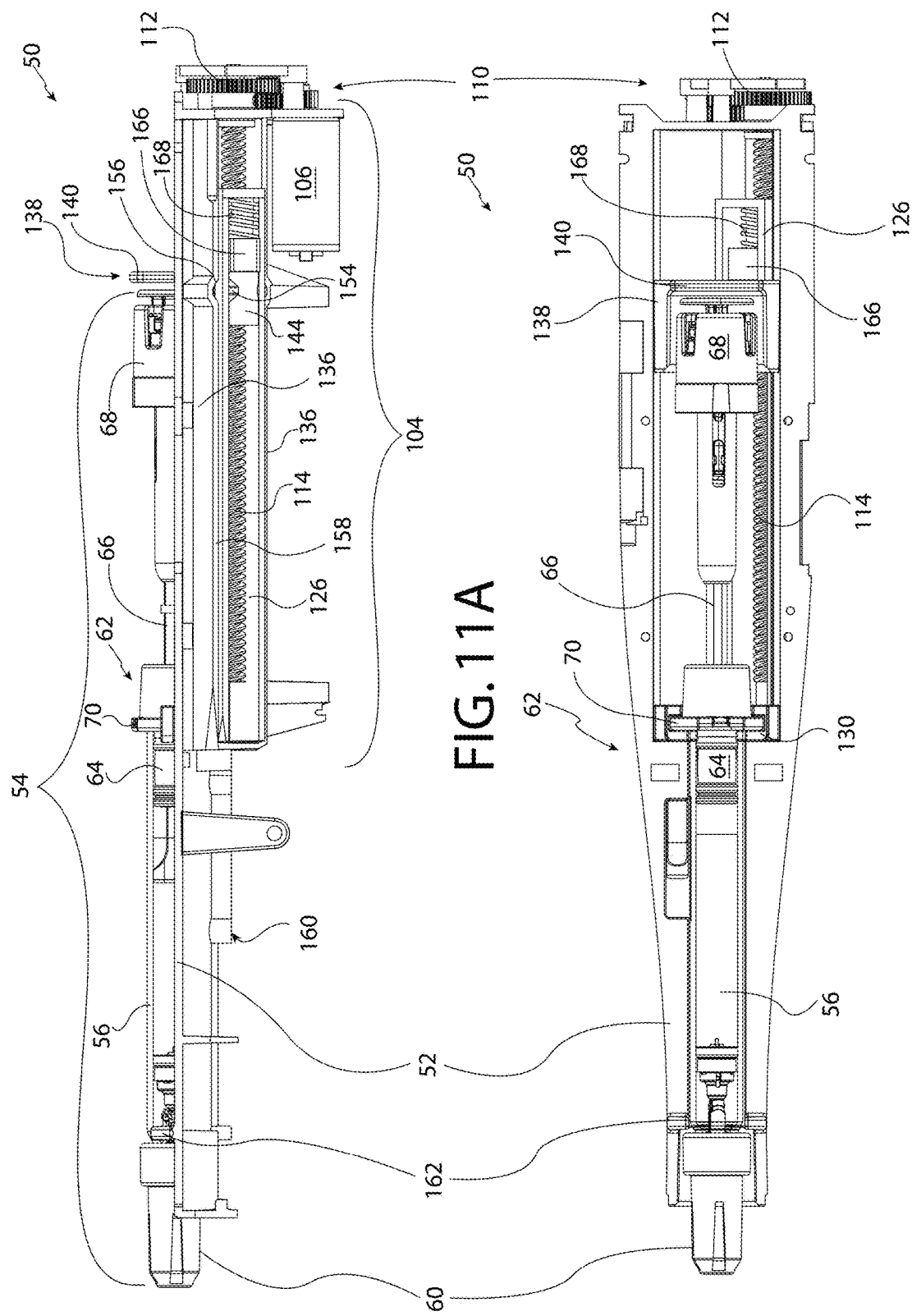

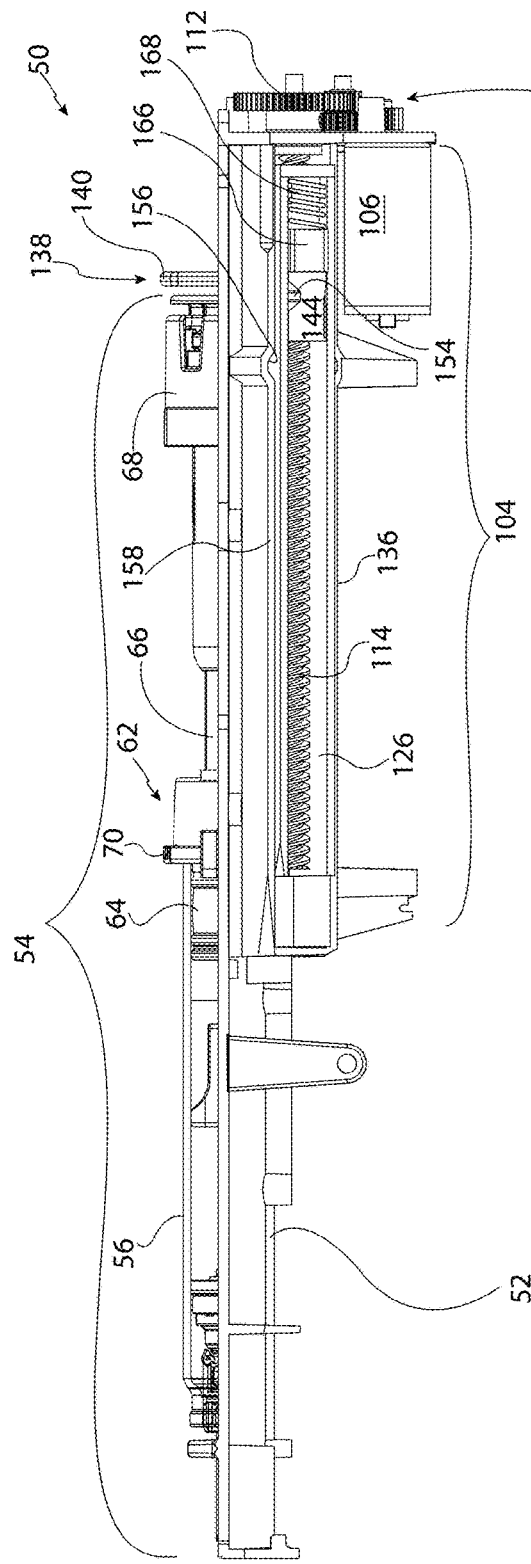
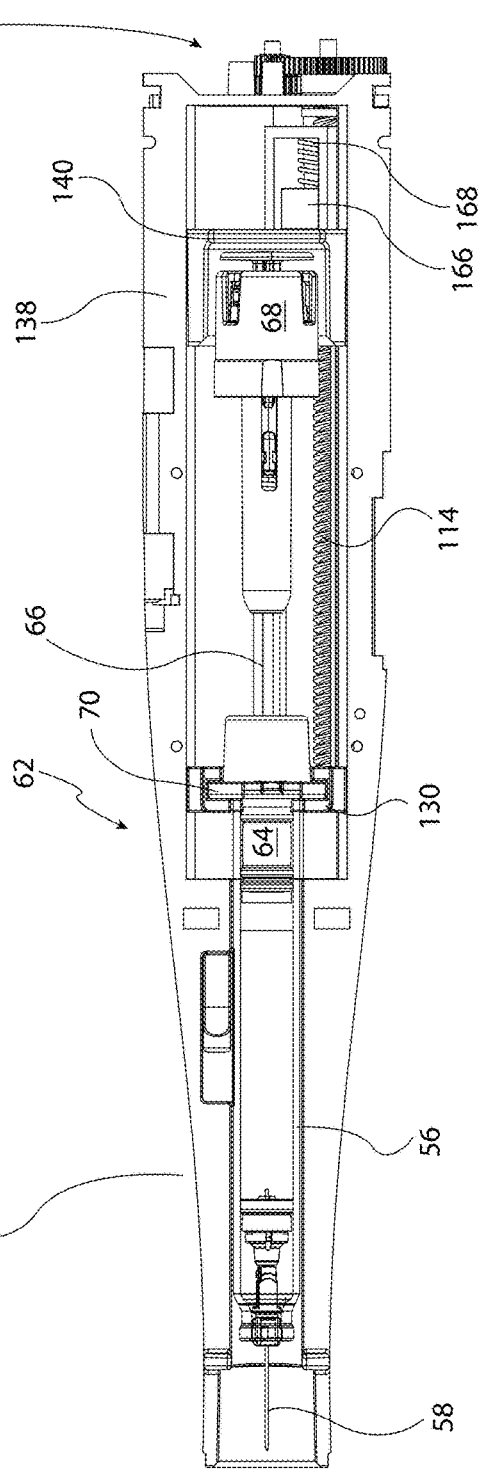
FIG. 12A
FIG. 12B

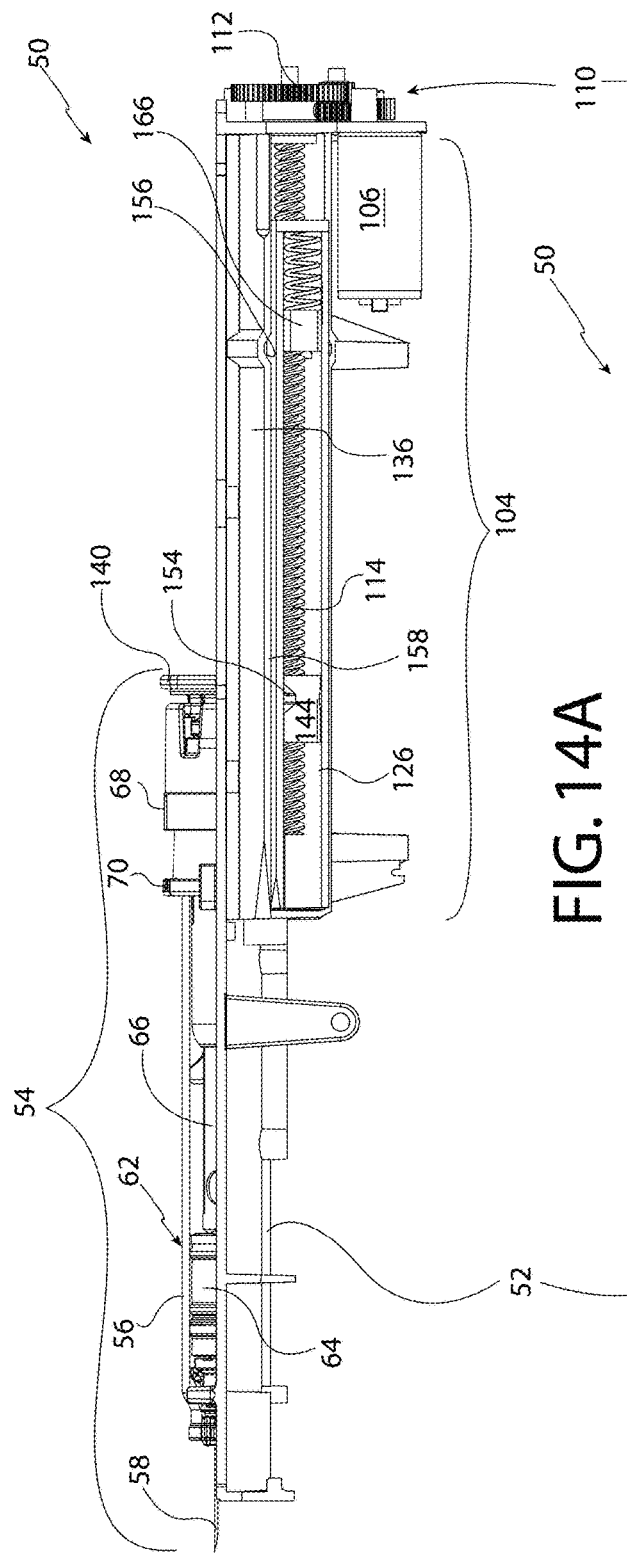
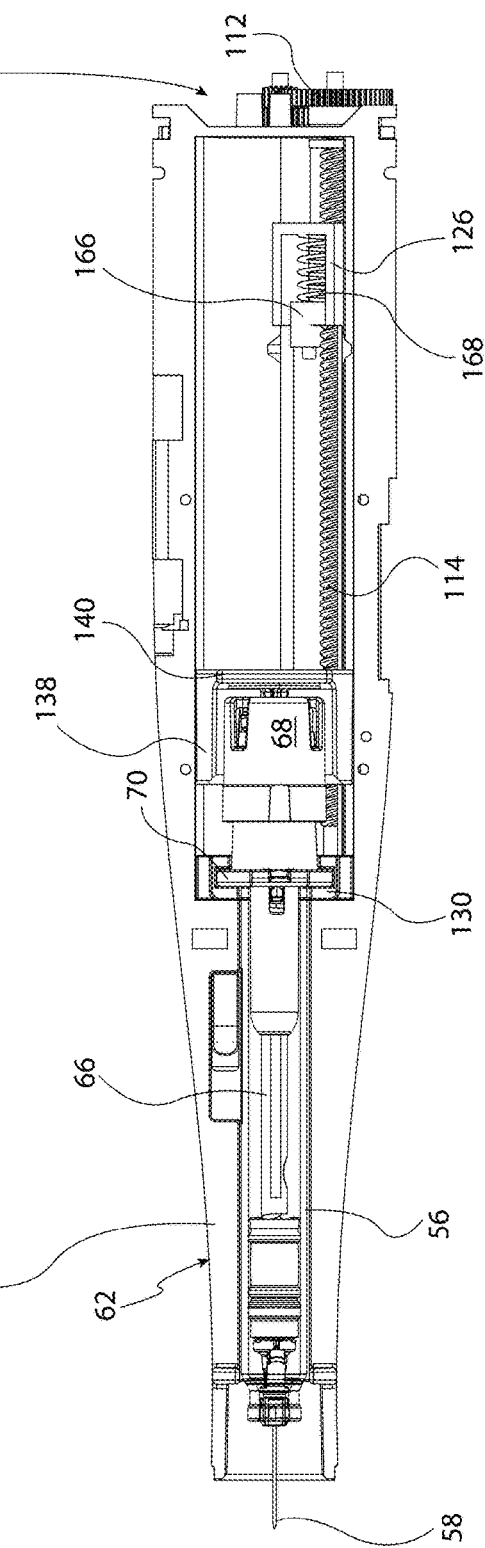
FIG. 14A
FIG. 14B

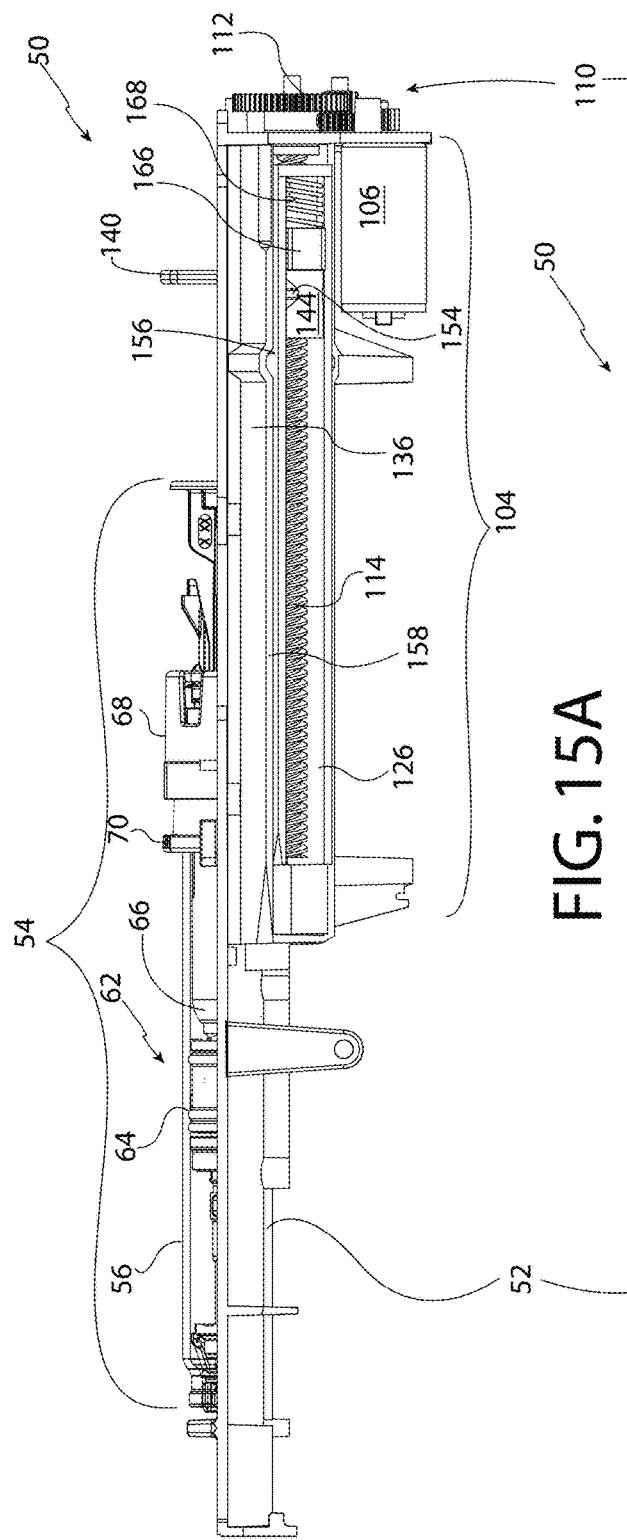
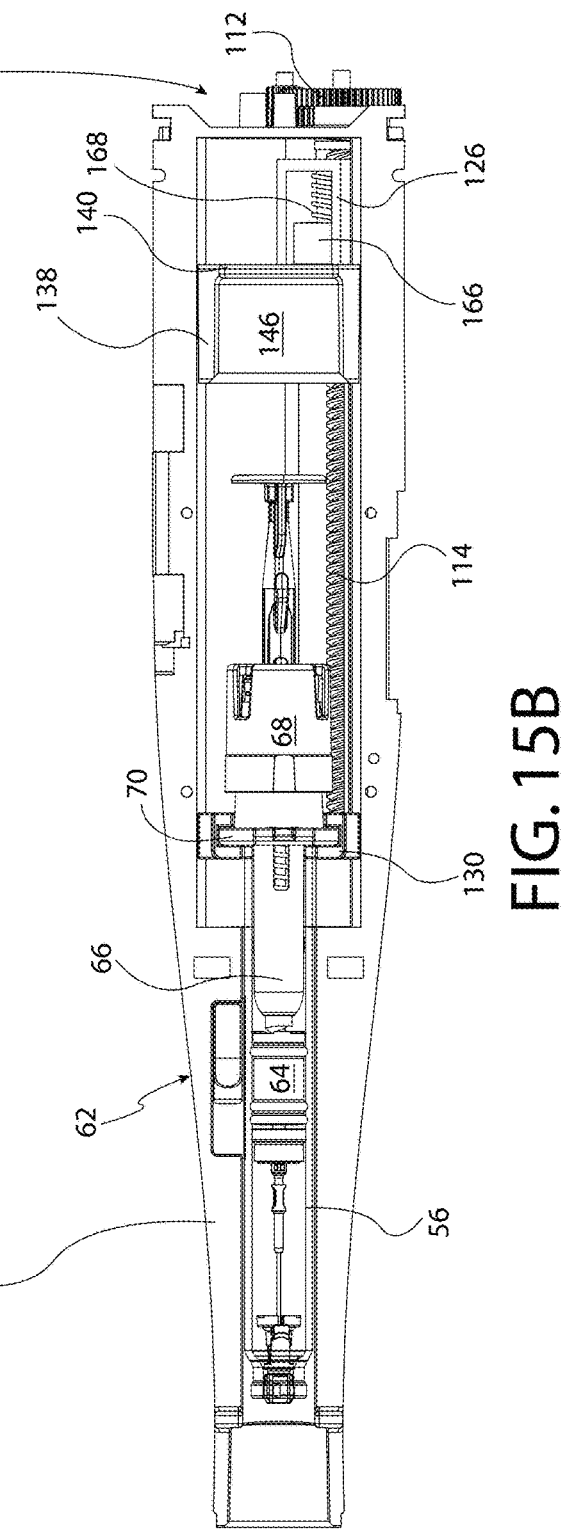
FIG. 15A
FIG. 15B

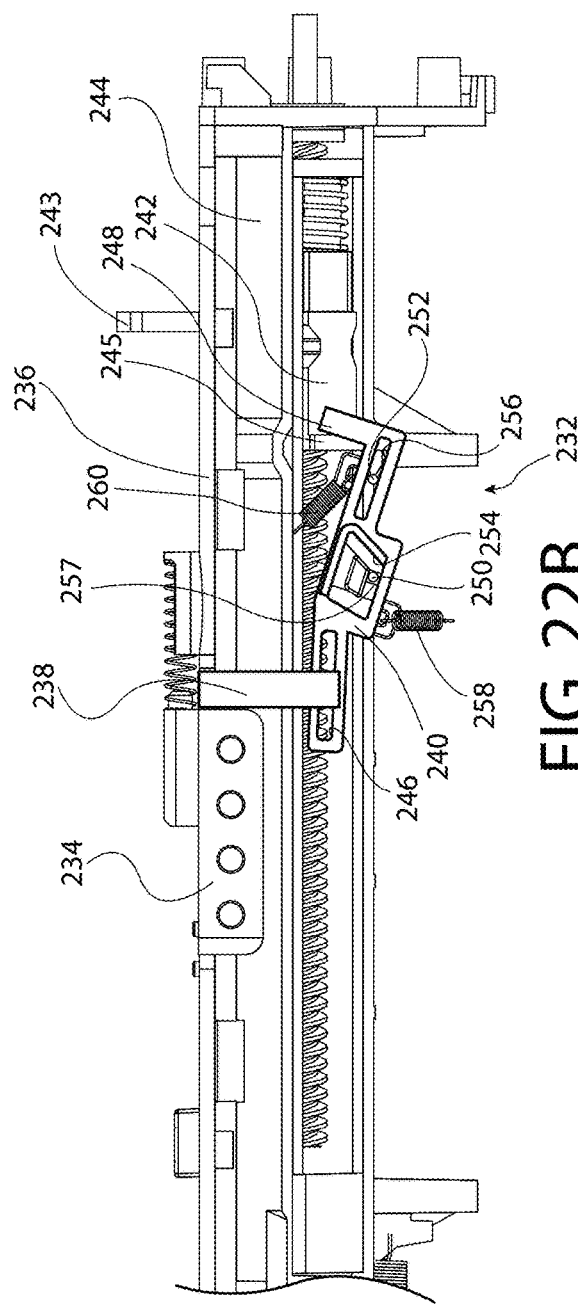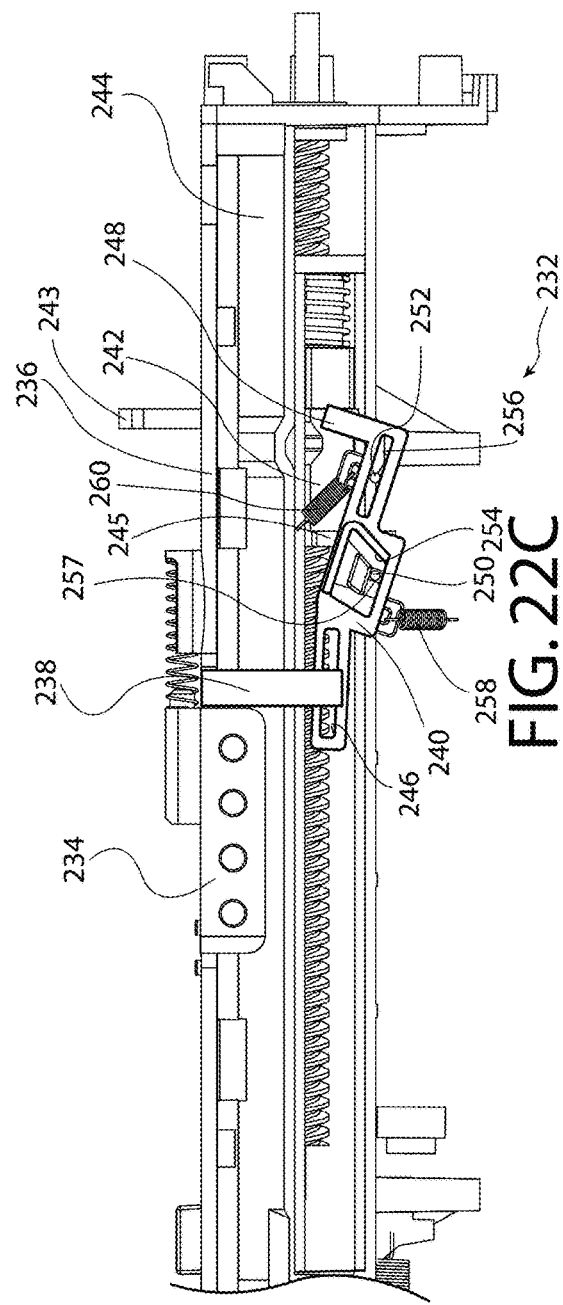

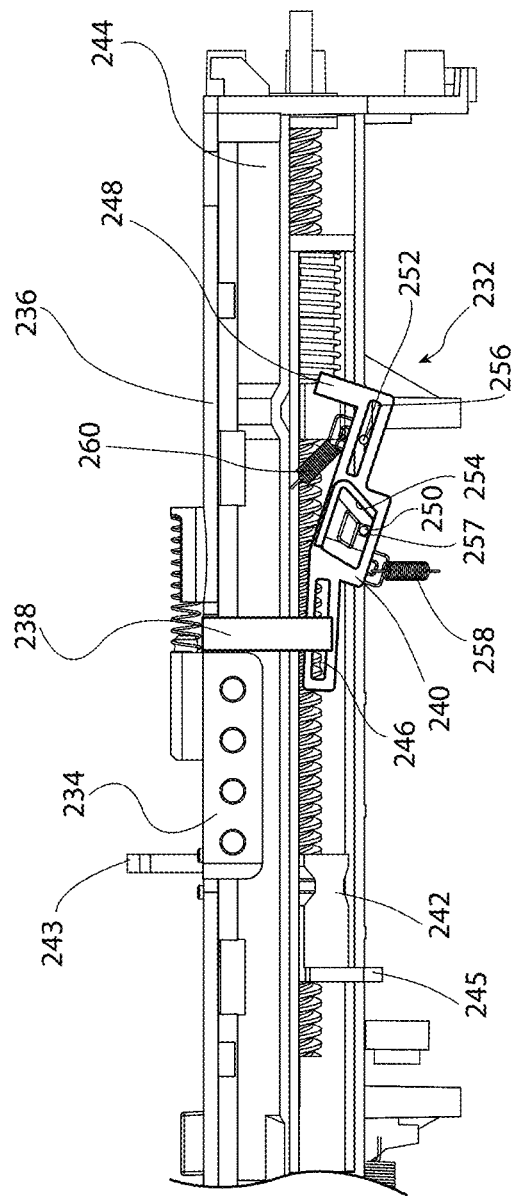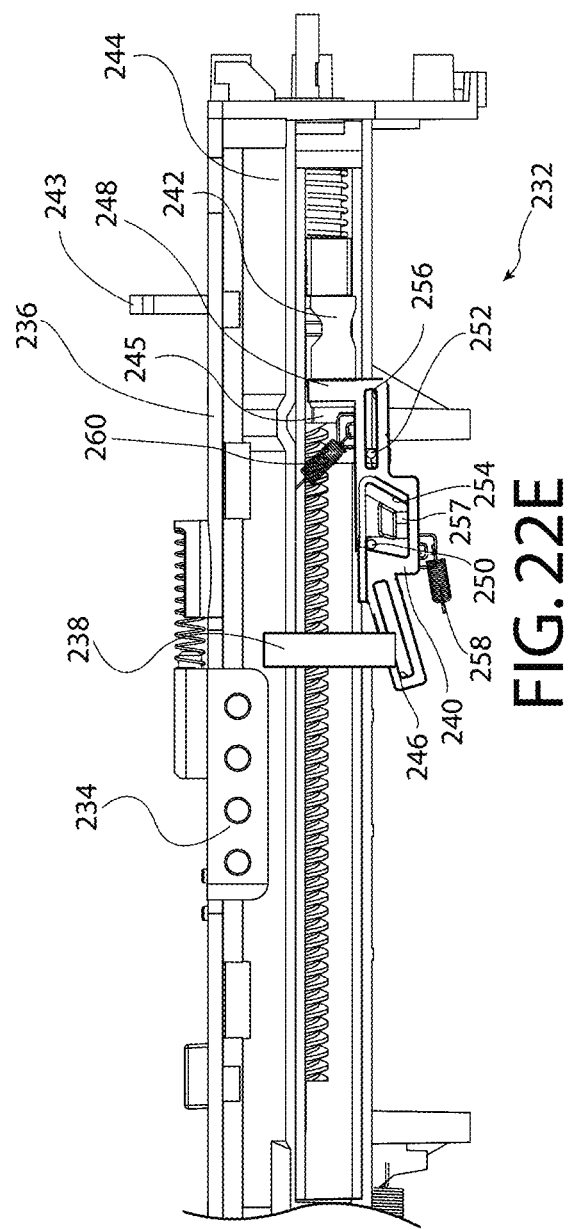

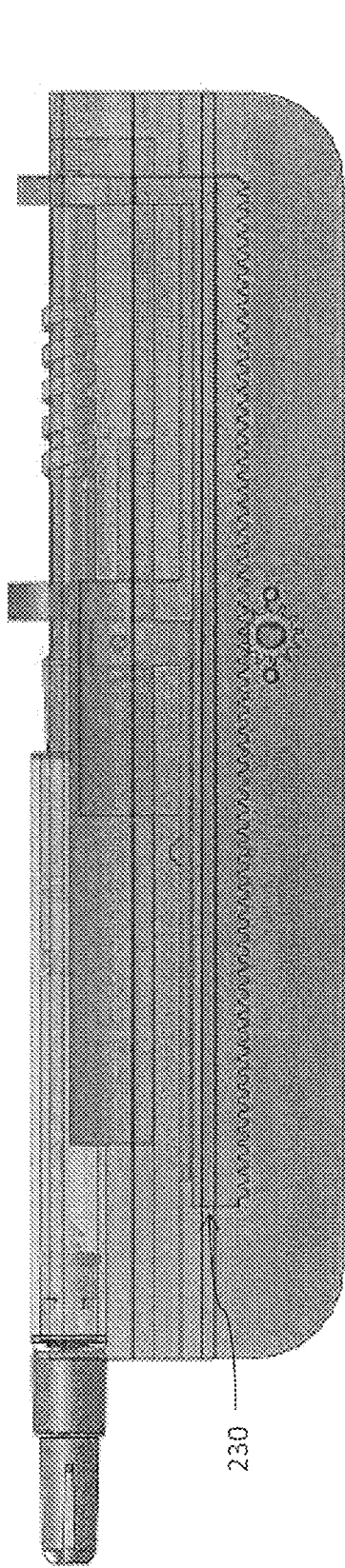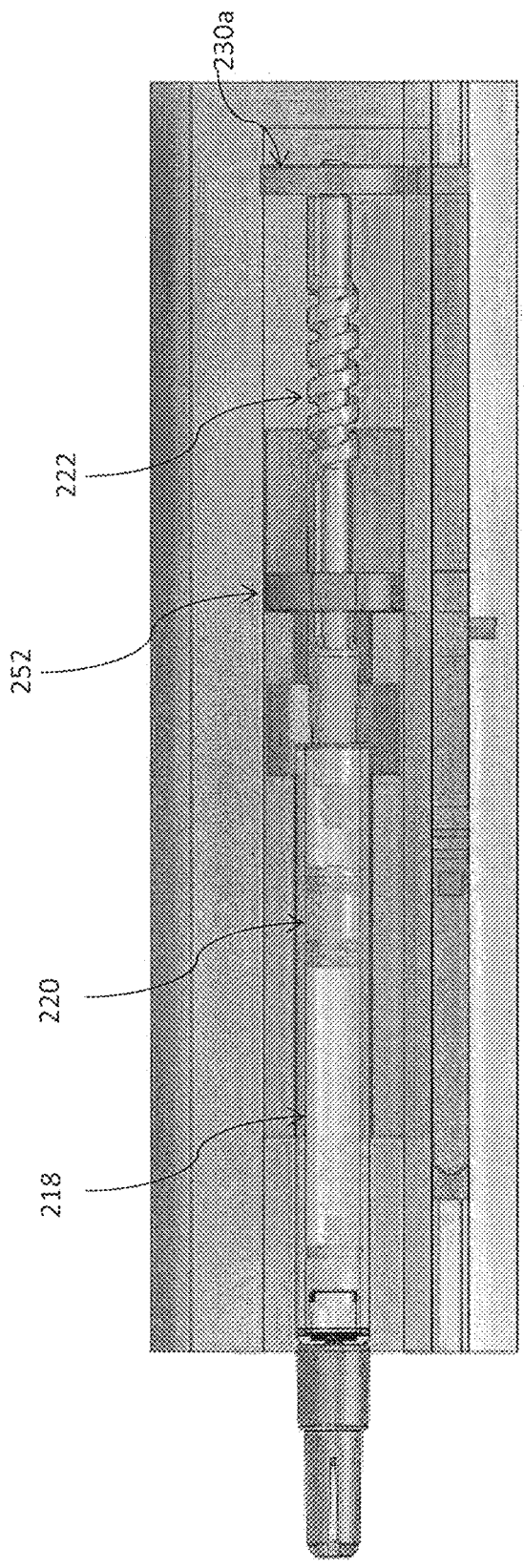

DRIVE CONTROL MECHANISMS AND AUTOMATIC INJECTORS FOR INJECTABLE CARTRIDGES

CROSS-REFERENCE TO RELATED APPLICATIONS

This application is a continuation of U.S. application Ser. No. 14/572,161, filed Dec. 16, 2014, which is a continuation of U.S. application Ser. No. 13/934,958, filed Jul. 3, 2013, now U.S. Pat. No. 8,920,374, issued on Dec. 30, 2014, which claims the benefit of U.S. Provisional Patent Application No. 61/683,499, filed Aug. 15, 2012, and U.S. Provisional Patent Application No. 61/668,303, filed Jul. 5, 2012. The entire teachings of the above applications are incorporated herein by reference.

FIELD OF THE INVENTION

The present invention relates to reusable automatic injection devices. More specifically, the embodiments of the present invention relate to electro-mechanical automatic injection devices which utilize motor-driven drive mechanisms, incorporate replaceable injection syringes, and perform one or more of the steps of: preparation and alignment of the syringe for injection, removal of the safety cap, needle injection and drug dose delivery, and needle and/or syringe retraction. The present invention also relates to drive mechanisms for reusable automatic injection devices, methods for manufacturing such devices, and their methods of use.

BACKGROUND OF THE INVENTION

Manually activated pre-filled cartridges are commercially available from a variety of manufacturers, including the owner and assignee of the present invention. The owner and assignee of the present invention has developed a syringe which offers a unique and elegant integrated mechanism for retraction of the needle and/or syringe. Currently visual, tactile or audible indicators are generally linked to the end of stroke or some other mechanical mechanism and not to the end of dose. The integrated needle retraction syringe retracts the needle into the barrel, removing it from the patient's skin, once the dose is complete.

Pre-filled cartridges are used in the administration of drug solutions, drug suspensions, vaccines, medicinal therapies, and any other liquid medicament by parenteral injection. Such pre-filled cartridges include a primary drug chamber, a hypodermic needle permanently affixed to and in fluid communication with the drug chamber, and a piston slidably received in the drug chamber. The pistons of the pre-filled cartridges often include a plunger sub-assembly, which may include a plunger inner and a plunger outer, to force the liquid medicament from the needle. Pre-filled cartridges are typically prepared by pharmaceutical companies or sterile filling contractors in a sterile filling room in which the drug and the cartridge are brought together in a sterile manufacturing environment wherein all components and drug solutions are isolated from microbial contamination.

In contrast to manually activated pre-filled cartridges, automatic injection devices, commonly known as "auto-injectors," are also available. Such auto-injectors, once triggered by the user, use an automatic mechanism to insert a hypodermic needle into the recipient's flesh at the injection site and force the liquid medicament out of a medicine compartment, through the hypodermic needle, and into the recipient. In addition to automatic needle insertion and dose delivery, some auto-injectors also incorporate retraction mechanisms to automatically retract the needle after use. Auto-injectors have proven particularly useful in allowing the medically untrained user to administer a parenteral injection, and can provide both psychological and physical advantages to patients.

Patients needing to inject medication for chronic disease management have used auto-injectors since the first reusable auto-injector was introduced in the 1990s. An auto-injector provides protection for the primary container, generally a pre-filled syringe, and offers an easy way for automatic injection of medication. These devices offer increased convenience and autonomy for patients as well as providing a competitive advantage to the pharmaceutical partner through device differentiation and increased sales through compliance of the patient to their therapy. Auto-injectors may also be beneficial in delivering large volumes (up to 1 mL currently) and viscous drugs. Auto-injectors also work to prevent needle stick injuries by housing the needle within a chamber, inserting the needle into the patient for drug introduction, then retracting the needle back into the housing utilizing, for example, reverse drive mechanisms.

Some auto-injectors have been designed to accept commercially available, manually activated pre-filled cartridges. Such configurations may be made in the form of cartridges for auto-injectors (e.g., reusable auto-injectors) or single-use auto-injectors. The syringes developed and manufactured by the owner and assignee of the present invention offer unique and elegant integrated retraction mechanism for needle safety. A number of different pre-filled syringes and cartridge configurations may be utilized in such auto-injectors, including those sold by the assignee and owner of the present invention under the trade name "Unifill" and covered by one or more of the following: U.S. Pat. Nos. 6,083,199, 7,500,967, 8,021,333, 8,002,745, 8,114,050, 8,052,654, 7,935,087, and 8,167,937; U.S. Patent Pub. No. 2011/0015572; and International PCT App. Nos. PCT/AU2010/001505, PCT/AU2010/001677, and PCT/AU2011/000515, all of which are incorporated herein by reference, in their entirety, for all purposes.

BRIEF SUMMARY OF THE INVENTION

The present invention relates to novel automatic injection devices for drug delivery with incorporate a multifunctional drive control mechanism. The components of the automatic injection devices are configured for repeatable functionality. Accordingly, the automatic injectors of the present invention may be single-use devices but are, preferably, utilized as reusable automatic injectors. Accordingly, a number of single-use syringes may be employed as cartridges with the automatic injectors of the present invention. The reusable auto-injectors of the present invention could be adapted for use with any type of retractable or safety syringe, but for simplicity, the invention is described when using a syringe similar to those sold by the owner and assignee of the present invention under the trade name "Unifill." The automatic injectors are also designed to accept a variety of syringes as drug-container cartridges.

The novel incorporation of the drive control mechanisms into the automatic injectors of the present invention enables a single motor and gear to drive the function of multiple components, which may include the steps of: preparation and alignment of a cartridge for injection, needle injection, drug dose delivery, and syringe and/or needle retraction. Optionally, the automatic injector may also perform the step of, before needle injection, removal of a safety cap or needle shield from the cartridge. Furthermore, optionally, the automatic injector may be configured to adjust the dose volume, such as by expending a portion of the drug dosage to a reservoir, prior to needle injection and drug dose delivery into a user. Utilizing a single drive control mechanism to control multiple device stages greatly simplifies the functionality of the automatic injector and improves the reliability, operation, and manufacturing cost of the reusable automatic injector. Additionally, the novel automatic injectors of the present invention are capable of repeatedly performing these tasks, making them reusable automatic injectors. Embodiments of the novel automatic injectors of the present invention may be capable of accomplishing all of these advantages while also maintaining an appearance and size comparable to existing products in the market. The simplicity and reusability of these automatic injectors facilitate ease-of-use and patient acceptance, both critical metrics for overall patient care and at-home use of the automatic injectors.

In one embodiment, the present invention provides a drive control mechanism for an automatic injector which includes a drive screw, a cartridge carrier, a plunger carrier, and one or more control transfer instruments. A motor with a gear train, including one or more gears, connected, either directly or indirectly, to the drive screw may be used to control the motion of the cartridge carrier and the plunger carrier.

The control transfer instruments may be, for example, a spherical ball, a cylinder, a disc or chip, or similar instruments that may freely move between the other components of the drive control mechanism. The control transfer instrument may preferably be cylinders (e.g., "pucks"). For simplicity, the control transfer instruments may be referred to herein as the "puck" or "pucks," though the actual shape and dimensions may vary from that of standard cylindrical objects. The transfer instrument functions to control the action of the components of the drive control mechanism by locking between two objects and causing them to move, or stay in a fixed position, as one unit. The transfer instrument may be retained in an annular space within, or between, the components of the drive control mechanism. In an embodiment, the plunger carrier contains a plunger carrier recess, while the cartridge carrier contains a channel, within both of which the transfer instrument may movably reside to control the operation of the drive control mechanism. Optionally, additional components may be utilized to retain the transfer instrument in a position from which it can control the control transfer function. For example, a guide having a guide recess may be employed for this purpose.

In an embodiment, the drive control mechanism for an automatic injector includes a drive screw, a cartridge carrier, a plunger carrier, a guide, and two control transfer instruments. The control transfer instruments may be a number of different shapes including, for example, pucks. The transfer instruments may be retained in annular spaces within, or between, the components of the drive control mechanism. The plunger carrier contains plunger carrier recesses, the cartridge carrier contains channels, and the guide has guide recesses for each transfer control instrument to interact with to control the operation of the drive control mechanism.

For example, in an initial stage, the components of the drive control mechanism are aligned such that the one or more control transfer instruments are allowed to freely pass between the guide recess and the plunger carrier recess through the channel of the cartridge carrier. When there are two or more control transfer instruments, there are corresponding guide recesses, channels, and plunger carrier recesses for each control transfer instrument. The plunger carrier recess and the guide recess can be a number of different configurations. In one embodiment of the present invention, the plunger carrier recess and the guide recess are symmetrical carve-outs of their respective components. Each of the recesses may be, for example, ramped to force the motion of the transfer instrument "out" into the guide recess or "in" into the plunger carrier recess. As the drive screw is caused to move axially, by operation of the motor and interaction with a gear or transmission assembly, the transfer instrument may be forced out from the plunger carrier recess into position between the guide recess and the channel of the cartridge carrier. At another stage of operation the guide recess may align with the channel of the cartridge carrier. By interaction of other aspects of the guide and the cartridge carrier, as described further below, the transfer instrument may be caused to move out of the guide recess and into position between the plunger carrier recess and the channel of the cartridge carrier. This alignment may cause the plunger carrier and the cartridge carrier to move as one unified unit. While the plunger carrier and the cartridge carrier are movable objects, the guide remains a fixed object throughout the operation of the drive control mechanism.

In another embodiment, the present invention provides an automatic injector which includes a housing having a guide, a drive control mechanism, a transmission assembly, a motor, and an energy source. The automatic injector may also contain certain standard features such as, for example, a microprocessor or similar control system which are known to an ordinarily skilled artisan. The housing may further include a cartridge cover. The drive control mechanism may include a number of components, including a drive screw, a cartridge carrier, a plunger carrier, and one or more control transfer instruments. The cartridge carrier interfaces and connects with a cartridge, such as a syringe, which holds a drug treatment for delivery to a patient. More particularly, a cartridge connection feature of the cartridge carrier connects with a corresponding aspect of the cartridge. This can be, for example, a tongue-and-groove connection as is known in the art. The cartridge connection feature and cartridge carrier may be separate components which are connected or are one unified component. The automatic injector may further comprise certain optional components such as, for example, a cartridge sensor and a patient sensor, which are described further below.

The motor may be an electric motor that is coupled with and powered by the energy source. The energy source may be, for example, a disposable battery or a rechargeable battery. The motor, drive control mechanism, and other components of the automatic injector may be employed to provide the force required for multiple injections over an extended period. A commercially available electric motor with both forward and reverse output shaft rotation may be used with a programmable controller, such as a microprocessor, to control the stages of operation required to perform the injection of the medicament and the retraction of the needle and/or syringe.

The reusable auto-injector could be adapted for use with any type of retractable or safety syringe, but for simplicity, the invention is described when using a syringe similar to those sold by the owner and assignee of the present invention under the trade name "Unifill." Because the components of the automatic injector and the drive control mechanism are able to repeatedly load, inject, and eject drug cartridges for injection of drug treatments to a patient, they are considered reusable automatic injectors.

In another embodiment, the present invention relates to the method for manufacturing automatic injectors. The method includes the steps of assembling a drive control mechanism which includes a drive screw, a plunger carrier, a cartridge carrier, and one or more control transfer instruments. The drive control mechanism may further include a guide having one or more guide recesses, one or more recess on the plunger carrier, and one or more channels within the cartridge carrier. The one or more control transfer instruments may be, for example, a spherical ball, a cylinder, a disc or chip, or similar instruments that may freely move between the other components of the drive control mechanism, but are preferably cylindrical pucks. These components are sized and configured such that the control transfer instrument is retained within the drive control mechanism and the guide. For example, the cartridge carrier may be a thin object having rectangular bores through it as channels. The transfer instruments may reside within the channels, but would be prevented from moving laterally along the axial plane of the carrier because they are retained on all four sides. The dimensions of the transfer instruments are such that the transfer instruments are always removably engaged with two components of the drive control mechanism and/or guide simultaneously. The method further includes the step of attaching a guide and a housing to the drive control mechanism. The method may further include the steps of attaching one or more of: an energy source, a motor, a transmission assembly, and a control system such as a microprocessor, wherein the transmission assembly is made to contact the drive screw. An injector or cartridge cover may also be attached to the automatic injector to facilitate loading and ejection of the cartridges.

In yet another embodiment, the present invention relates to a method of use for an automatic injector. The method includes the steps of: inserting a cartridge into a cartridge carrier contained in a housing of the automatic injector and activating the automatic injector to initiate, optionally, one or more of: removal of a needle shield, injection of a needle into a patient, delivery of drug through the needle to the patient, retraction of the needle from the patient into the housing, and removal of the cartridge from the cartridge carrier. Furthermore, optionally, the method of use may include the step of expending a portion of the drug dosage to a reservoir or to the environment, prior to needle injection and drug dose delivery into a user, in order to reduce or adjust drug volume. The method may further include the steps of opening a cartridge cover to access an interior of the automatic injector prior to the insertion of a cartridge into the cartridge carrier, and the step of closing the cartridge cover after the cartridge has been loaded into the cartridge carrier. The method may similarly include the step of opening the cartridge cover to access an interior of the automatic injector after the retraction of the needle to remove the used cartridge. The user may optionally reattach the needle shield to the cartridge after the syringe has been used (i.e., drug delivery has completed). After the used syringe has been removed from the cartridge carrier of the automatic injector, the automatic injector is reset and ready to accept another cartridge.

The embodiments shown and detailed herein disclose only a few possible variations of the present invention; other similar variations are contemplated and incorporated within the breadth of this disclosure. As would be readily appreciated by an ordinarily skilled artisan, a number of parameters, shapes, and dimensions described above may be modified while remaining within the breadth and scope of the present invention.

An automatic injector is adapted to receive a cartridge that includes a barrel, a needle, and a plunger assembly including a plunger seal. The cartridge defines a longitudinal axis. The automatic injector includes a housing, a cartridge carrier, and a plunger carrier. The cartridge carrier is adapted to receive at least a portion of the cartridge. The cartridge carrier is disposed for movement relative to the housing in a direction parallel to the longitudinal axis of the cartridge. The plunger carrier is disposed for movement relative to the cartridge carrier. The plunger carrier is disposed to confront and impart movement at least a portion of the plunger assembly. At least one transfer instruments is disposed to selectively couple the cartridge carrier to the plunger carrier for movement therewith. An elongated drive device is coupled to the plunger carrier. The elongated drive device is disposed to provide movement of the plunger carrier in a direction parallel to the longitudinal axis of the cartridge.

A method of operating an automatic injector to inject a fluid from a cartridge includes disposing the cartridge in the automatic injector with at least a portion of a barrel disposed within a cartridge carrier, and a plunger assembly disposed for confrontation with a plunger carrier, a needle end of the cartridge defining a distal end of the automatic injector and the opposite end of the cartridge defining a proximal end of the automatic injector, coupling the cartridge carrier to the plunger carrier, utilizing a single drive mechanism to move the plunger carrier and the cartridge carrier to advance the cartridge in an axial direction toward the distal end, decoupling the cartridge carrier from the plunger carrier, utilizing the drive mechanism to move the plunger carrier in the axial direction toward the distal end to dispense the fluid, and retracting the plunger carrier in an axial direction toward the proximal end.

A method of operating an automatic injector includes disposing a first cartridge in a housing of the automatic injector, actuating the automatic injector to dispense fluid from the first cartridge, removing the first cartridge from the housing, disposing a second cartridge in the housing, and actuating the automatic injector to dispense fluid from the second cartridge.

BRIEF DESCRIPTION OF THE DRAWING(S)

The following non-limiting embodiments of the invention are described herein with reference to the following drawings, wherein:

FIG. 1 shows an isometric view of the reusable automatic injector, according to one embodiment, with an optional cartridge cover of the housing closed and the injector ready for operation.

FIG. 2 shows an isometric view of the reusable automatic injector, according to one embodiment, with an optional cartridge cover of the housing open for loading of a syringe cartridge.

FIG. 3 is a fragmentary view of a distal end of a reusable automatic injector with the cartridge cover in a closed position.

FIG. 4 is an exploded isometric view of a housing and aspects of a drive control mechanism according to an embodiment.

FIG. 6 shows an isometric view of the components of the drive control mechanism, motor, and transmission assembly according to one embodiment of the present invention.

FIGS. 7-8 show top and bottom views, respectively, of the components shown in FIG. 6.

FIG. 9 shows an isometric view of the cartridge carrier of the drive control mechanism, according to one embodiment of the present invention.

FIGS. 10A-10E show expanded views of components of the drive control mechanism of the reusable automatic injector, according to the embodiment shown in FIGS. 11-15, as they progress through the stages of: syringe cartridge loading, removal of rigid needle shield, needle injection, drug dose delivery, and needle retraction.

FIG. 11A is a side view of the reusable automatic injector, according to one embodiment of the present invention, shown in the syringe cartridge loading configuration.

FIG. 11B is a top view of the reusable automatic injector shown in FIG. 11A.

FIG. 12A is a side view of the reusable automatic injector, according to one embodiment of the present invention, shown in the needle shield removal configuration.

FIG. 12B is a top view of the reusable automatic injector shown in FIG. 12A.

FIG. 14A is a side view of the reusable automatic injector, according to one embodiment of the present invention, shown in the drug delivery configuration.

FIG. 14B is a top view of the reusable automatic injector shown in FIG. 14A.

FIG. 15A is a side view of the reusable automatic injector, according to one embodiment of the present invention, shown in the syringe/needle retraction configuration.

FIG. 15B is a top view of the reusable automatic injector shown in FIG. 15A.

FIGS. 22A-22E are side elevational views of a housing illustrating a cartridge cover release safety mechanism according to aspects of the invention.

FIG. 23A is a side view of the reusable automatic injector, according to another embodiment of the present invention having a permanent plunger rod;

FIG. 23B is a top view of the reusable automatic injector shown in FIG. 23A.

DETAILED DESCRIPTION OF THE INVENTION

Figure 5:
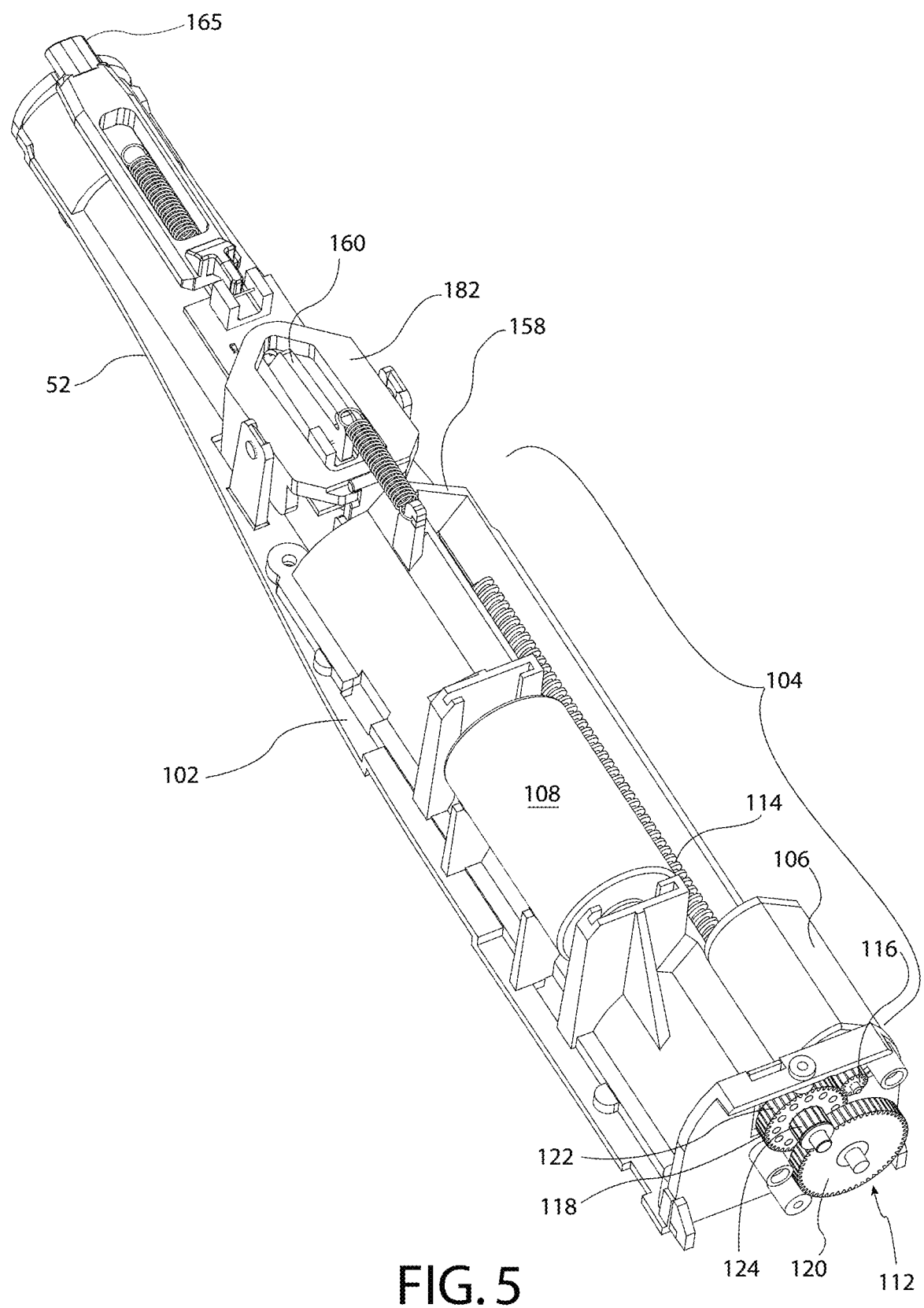
FIG. 5 shows an isometric view of the bottom of a reusable automatic injector according to the embodiment shown in FIGS. 1-5.

The embodiments of the present invention relate to automatic injection devices for drug delivery. The components of the automatic injection devices are configured for repeatable functionality, and the automatic injectors are designed to accept a variety of drug containers, such as syringes, as cartridges. For the purposes of this disclosure, the term "cartridge" will refer generically to both syringes, which include a plunger rod for administration of a medicament from a barrel by movement of a plunger seal, and medicament containing barrels that do not include a plunger rod for activation of a plunger seal.

The automatic injectors of the present invention may be single-use devices but are, preferably, utilized as reusable automatic injectors. More specifically, the embodiments of the present invention relate to electro-mechanical automatic injection devices which utilize motor-driven drive mechanisms, incorporate replaceable injection syringes, and perform one or more of the steps of: preparation and alignment of a cartridge for injection, removal of a safety cap or needle shield, needle injection, drug dose delivery, and syringe and/or needle retraction. The novel incorporation of the drive control mechanisms into the automatic injectors of the present invention enables a single motor and transmission assembly to drive the function of multiple components, thereby simplifying the functionality of the device and improving the reliability, operation, and manufacturing cost of the reusable automatic injector. The present invention also relates to drive mechanisms for automatic injection devices, methods for manufacturing such devices, and their methods of use. Furthermore, optionally, the automatic injector may be configured to adjust the dose volume, such as by expending a portion of the drug dosage to a reservoir, prior to needle injection and drug dose delivery into a user.

As used herein to describe the drive mechanisms, automatic injectors, cartridges, or any of the relative positions of the components of the present invention, the terms "axial" or "axially" refer generally to a longitudinal axis "A" around which reusable automatic injector is preferably positioned although not necessarily symmetrically there-around. The terms "proximal," "rear," "rearward," "back," or "backward" refer generally to an axial direction in the direction of the plunger rod or transmission assembly. The terms "distal," "front," "frontward," "depressed," or "forward" refer generally to an axial direction in the direction of the needle or rigid needle shield. The term "laterally" refers to a direction in a plane normal to a longitudinal axis "A." The term "radial" refers generally to a direction normal to axis A.

As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration.

"Fluid" refers primarily to liquids, but can also include suspensions of solids dispersed in liquids, and gasses dissolved in or otherwise present together within liquids inside the fluid-containing portions of cartridges. The terms "drug," "medicine," and "medicament" are used to refer to any substance that is administered from a cartridge through a needle or cannula, and is not limited to pharmaceutical substances, but may include, for example, vitamins or minerals.

As used herein, the terms "automatic injector" and "auto-injector" are meant to refer to the same reusable devices, which may also be referred to by the acronym "RAI". "Puck" is used herein to describe a component of the drive control mechanism, but the term is not limited to such a shape and, in one or more embodiments of the present invention, may be a spherical ball, cylinder, conoid, or other functional shape that can be caused to move freely when acted upon by one or more adjacent surface(s).

Turning first to FIGS. 1 and 2, there is shown an automatic injector 50 according to the invention. The automatic injector 50 includes a housing 52 adapted to receive and support a syringe or cartridge 54 for injection, as well as various components of the injection system. A variety of cartridges 54 may be utilized in the reusable automatic injector 50 of the present invention, including those having automatic retraction features. For example, a safety syringe with integrated needle retraction may be used with the reusable automatic injector 50. One example of such a cartridge 54 in the form of a safety syringe is illustrated in FIG. 2 and in FIGS. 11A-15B, and includes a barrel 56, a needle 58, a rigid needle shield 60, and a plunger assembly 62 including a plunger seal 64, a plunger rod 66, and a plunger head 68. The cartridge 54 includes a longitudinal axis A. In the illustrated embodiment, the barrel 56 of the cartridge 54 includes an enlarged finger flange 70, such as is commonly used in standardized barrel 56 designs. The cartridge 54 can be pre-filled with a drug or filled at-time-of-use by a user, that is, just prior to placement within the reusable automatic injector 50. Alternate embodiments of cartridges 54 may include, by way of example only, cartridges 54 having a barrel 56 sealed by a plunger seal 64, but having no plunger rod 66 (see, e.g., FIG. 21 and explanation below).

The housing 52 may optionally be covered by a cartridge cover 72, which may likewise be of any appropriate design. In order to allow the user to view the status of the automatic injector 50, the cartridge cover 72 may be entirely or partially translucent or transparent. Alternately, it may be entirely or partially opaque. The cartridge cover 72 of FIGS. 1 and 2 includes a window 74 that is disposed substantially adjacent the barrel 56 of a supported cartridge 54, allowing the user to view the status of drug delivery. Optionally, the window 74 or portion of the cartridge cover 72 adjacent the window may have dose indication markings to allow the user to identify the drug dose volume contained in the cartridge 54 prior to, during, and/or after drug delivery.

In the illustrated embodiment, the cartridge cover 72 is hinged to the housing 52, although an alternate arrangement may be provided. For example, the either the cartridge cover 72 or the housing 52 may include mating protrusions and the other of the cartridge cover 72 or the housing 52 may include detents for receiving the protrusions. Such protrusions and detents may be provided alone, or in conjunction with a hinge arrangement, and may be provided at any appropriate location between the housing 52 and the cartridge cover 72. In one such embodiment, as shown in FIG. 3, a distal detent 76 with mating protrusion 78 may be disposed at or substantially near the distal end of the automatic injector 50 to ensure that the distal end of the cartridge cover 72 is held rigidly to the housing 52, and provide secure closure along substantially the entire contacting surface between the cartridge cover 72 and the housing 52. While the housing 52 and cartridge cover 72 may be formed as separate components, the cartridge cover 72 and the housing 52 may alternatively be formed as a single unit, coupled by a so-called living hinge (not illustrated).

The automatic injector 50 may further include a casing body 80, which provides a smooth outer appearance to the housing 52. The casing body 80 may be formed as a separate structure from the housing 52 that presents an internal chamber that receives the housing 52, or the housing 52 and the casing body 80 may be formed as a single unit. It will be appreciated that, when the automatic injector 50 includes a cartridge cover 72, the cartridge cover 72 may be coupled to the housing 52 by way of the casing body 80. That is, the cartridge cover 72 may be coupled to the casing body 80, which receives the housing 52. As with the housing 52 and the cartridge cover 72, the casing body 80 and the cartridge cover 72 may be formed separately, or as a single unit, connected, for example, by a living hinge (not illustrated).

In the embodiment illustrated in FIGS. 1 and 2, the cartridge cover 72 is held in a closed position over the housing 52 by a selectively actuable latch 86. In the illustrated embodiment, the cartridge cover 72 includes a protrusion 88 that is received by a recess 90 in the housing 52. A latch release 92 may be slid to the side or depressed to allow the cartridge cover 72 to be latched to or unlatched from the housing 52.

The automatic injector 50 may further include a user interface 96 with features such as a release actuator 98 that may be depressed to initiate operation of the automatic injector 50 or selection of other operative features. Other operative features may include, by way of example only, an identification of the adjustments based upon the needle 58 utilized in the cartridge 54, or volume of medicament carried in the cartridge 54 and the volume to be dispensed, as will be explained in greater detail below. The automatic injector 50 may further include one or more lights 100, or the like, indicating the state of operation of the automatic injector 50.

The housing 52 may be of any appropriate design, and may be formed as a unitary structure, or it may include a plurality of components. Referring to FIGS. 4 and 5, the housing 52 is an elongated frame 102 adapted to removably support a cartridge 54 along the upper surface or along structure associated with the housing 52. The housing 52 may further support one or more of the structures associated with the operation or usage of the automatic injector 50. More specifically, in the embodiment illustrated in FIG. 5, the housing 52 additionally supports a drive control mechanism 104 that controls movement of components of the cartridge 54 within the housing 52. The drive control mechanism 104, which will be described in greater detail below, may be operated by motor 106 powered by an energy source 108. While the motor 106 and energy source 108 are illustrated as being supported on the housing 52, they could alternately be otherwise supported, for example, within a casing body 80. The energy source 108 may be in a number of different configurations and a variety of sources including, for example, disposable batteries, or rechargeable and reusable batteries. A transmission assembly 110 couples the rotary motion of the motor 106 to the drive control mechanism 104.

The reusable automatic injector 50 may also contain certain standard features such as, for example, one or more control systems, such as a microprocessor (not specifically illustrated), may be used to control the timing and parameters of operation of the automatic injector 50. Operation of the control systems may optionally be based upon feedback from one or more sensors, or input received from the user by way of the user interface 96. For example, the automatic injector 50 may include features that are associated with the closure of the cartridge cover 72 to the housing 52, or the position of the latch release 92. In order to minimize the opportunity for inadvertent actuation of the automatic injector 50, an optional sensor may be utilized to signal whether the cartridge cover 72 is open or closed, allowing a control system associated with the automatic injector 50 to prevent actuation if the cartridge cover 72 is not closed. Similarly, structure of the automatic injector 50 or the control system may be designed to prevent opening of the cartridge cover 72, that is, movement of the latch release 92, unless the internal components are in one or more particular positions.

The microprocessor may be configured to receive feedback from the individual sensors, and to cause certain activity of the motor 106 and transmission assembly 110 based on varying feedback from one or more sensors. The attached figures exclude such control systems, as a number of different systems or configurations may be employed, but a control system should be understood as being optionally included. The control system, as would readily be appreciated by one having ordinary skill in the art, would accept some user activity at one or more system controls and interpret such activity by the user to activate the features of the reusable automatic injector 50. In at least one embodiment, the control system is a microprocessor located at the proximal end of the automatic injector 50 adjacent the transmission assembly 110 and the user interface 96 (shown in FIG. 2-10).

According to an aspect of embodiments of the invention, the automatic injector 50 provides predicable movement for actuation of a loaded cartridge 54. In some embodiments, the automatic injector 50 provides repeatable movement, such that the automatic injector 50 may be utilized repeatedly with a plurality of cartridges 54. In order to inject a patient, the automatic injector 50 proceeds through a plurality of stages that include movement of the needle 58 into a target tissue, and administration of an injection by movement of the plunger seal 64.

In order to provide longitudinal movement of components of the cartridge 54 relative to the housing 52, the housing 52 supports the drive control mechanism 104 that interfaces with the motor 106 via the transmission assembly 110. The transmission assembly 110 may have a number of configurations which enable it to transfer motion and energy from the motor 106 to the drive control mechanism 104. An exemplary transmission assembly 110 is shown in greater detail in FIGS. 5-8. FIGS. 7-8 show the components of the drive control mechanism 104 and transmission assembly 110 illustrated in the isometric views of FIGS. 5-6 from top and bottom viewing angles. The transmission assembly 110 includes a gear train 112 that transmits rotary motion from the motor 106 to an elongated drive device, here, a drive screw 114, that interfaces with the drive control mechanism 104. The elongated drive device, here, the drive screw 114, is disposed to impart movement to at least a portion of the plunger assembly 62 by way of the drive control mechanism 104. The drive control mechanism 104 will be described in greater detail below.

It will be appreciated that the gear train 112 may have a number of configurations which enable it to transfer motion and energy from the motor 106 to the drive screw 114. For example, the gear train 112 may be a simple gear or a pair of bevel gears that transfer motion from a motor 106 to a drive screw 114. Referring to FIGS. 5-8, in particular, in at least one embodiment of the present invention, the transmission assembly 110 includes a pinion gear 116 connected to the motor 106, a compound gear 118, and a drive gear 120. The compound gear 118 may have a primary gear surface 122 which engages the pinion gear 116, and a secondary gear surface 124 which engages the drive gear 120. The drive gear 120 is connected to the drive screw 114. It will be appreciated that as the motor 106 rotates the pinion gear 116 in a clockwise direction, for example, the teeth of the pinion gear 116 engage the teeth of primary gear surface 122 of the compound gear 118, rotating the compound gear 118 in a counterclockwise direction. As a result, the teeth of secondary gear surface 124 engage with the teeth of the drive gear 120 to rotate the drive gear 120, as well as the connected drive screw 114 in a clockwise direction.

This configuration of the transmission assembly 110 enables motion of the motor 106 to control motion of the drive screw 114 in a manner which minimizes the internal volume of the automatic injector 50 because both the motor 106 and drive screw 114 can be positioned in an axial alignment. As would be readily appreciated by a skilled artisan, motion of the drive screw 114 by the transmission assembly 110 is caused by the interaction between the teeth of the gears of the transmission assembly 110. The teeth of one or more of these gears may be radial to the center point of each gear, commonly referred to as "spur gears," or they be a number of other gear types known to one having ordinary skill in the art.

An exemplary drive control mechanism 104 is shown in more detail in FIGS. 6-9. The drive control mechanism 104 includes a cartridge carrier 126, a plunger carrier 138 disposed to provide longitudinal movement relative to the cartridge carrier 126, and a transfer instrument 150 disposed to control relative movement between the plunger carrier 138 and the cartridge carrier 126.

The cartridge carrier 126 includes an elongated frame 128 having a cartridge connection feature 130. In the illustrated embodiment, the elongated frame 128 includes a pair of rails 132 with the cartridge connection feature 130 disposed at a distal end thereof. The cartridge connection feature 130 is adapted to interface with and support a proximal end of the barrel 56 of the cartridge 54. In the illustrated embodiment, the cartridge connection feature 130 includes an internal channel 134 adapted to receive the enlarged finger flange 70 of the cartridge 54. The cartridge connection feature 130 may include, for example, a tongue-and-groove connection or any other removably engaging connection feature known in the art. It will be appreciated by those of skill in the art that an alternate coupling may be provided at the illustrated or an alternate position, so long as the movement of the cartridge carrier 126 in the proximal or distal direction results in a corresponding movement of the barrel 56 of the cartridge 54.

In order to provide for movement of the cartridge 54 to facilitate, for example, insertion of the needle 58 into target tissue, the cartridge carrier 126 is mounted for axial movement relative to the housing 52. In the illustrated embodiment, the housing 52 includes a pair of longitudinally extending rails 136 along which the elongated frame 128 of the cartridge carrier 126 ride. It will be appreciated, however, that the relative axial movement may be facilitated by any appropriate structural arrangement. In this way, during one or more stages of the operation of the automatic injector 50, such as the insertion and removal of a needle 58 from target tissue, the cartridge carrier 126 may move the barrel 56 of the loaded cartridge 54 in the proximal or distal direction relative to the housing 52.

To allow for administration of a medicament, the drive control mechanism 104 provides for the longitudinal movement of the plunger seal 64 within the barrel 56 of the cartridge 54. In the illustrated embodiment, the drive control mechanism 104 includes a plunger carrier 138 that receives the plunger head 68 connected to the plunger rod 66. The illustrated plunger carrier 138 includes an interface feature 140 that confronts at least a portion of a proximal end of the plunger assembly 62, here, the plunger head 68. In this way, movement of the plunger carrier 138 in the distal direction causes the plunger head 68 and the plunger rod 66 causes the plunger seal 64 to move in a distal direction within the barrel 56 to administer a medicament.

Returning to the embodiment illustrated in FIGS. 4 and 6-8, to dispense medication from the cartridge 54, the plunger carrier 138 is mounted such that operation of the motor 106 by way of the transmission assembly 110 and drive screw 114 results in longitudinal movement relative to the housing 52. As may best be seen in FIG. 4, the plunger carrier 138 includes an internally threaded bore 142 that is complimentary to the externally threaded drive screw 114. In the illustrated embodiment, the internally threaded bore 142 extends through a portion 144 of the plunger carrier 138 that is disposed between the rails 132 of the cartridge carrier 126 such that the a cradle 146 of the plunger carrier 138 rides along an upper surface of the rails 132 while portion 144 rides between the rails 132.

As the drive screw 114 rotates, the plunger carrier 138 travels in a longitudinal direction dependent upon the direction of the rotation of the drive screw 114 as well as the configuration of the threads on the externally threaded drive screw 114 and in the internally threaded bore 142. The interaction and rotation of the gears of the gear train 112, driven by the motor 106, drive the operation of the automatic injector 50 as they rotate the drive screw 114. For example, based upon the illustrated thread configuration and viewing the automatic injector 50 from the proximal end, clockwise rotation of the motor 106 causes the drive screw 114 to move the plunger carrier 138 of the injector 50 in the proximal direction relative to the housing 52 as the drive screw 114 rotates in a clockwise direction; conversely, counterclockwise rotation of the motor 106 causes the drive screw 114 to rotate in a counterclockwise direction to move the plunger carrier 138 in the distal direction relative to the housing 52. Should the drive screw 114 and the internally threaded bore 142 of the plunger carrier 138 each have an opposite thread configuration to that illustrated, the direction of movement of the plunger carrier 138 in the proximal or distal direction relative to the housing 52 would be the opposite.

In other words, operation of the motor 106 rotates the drive screw 114 by way of the transmission assembly 110, and rotation of the drive screw 114 moves the plunger carrier 138 in the longitudinal direction within the housing 52. In the illustrated embodiment, this movement of the plunger carrier 138 is likewise utilized to provide selective longitudinal movement to the cartridge carrier 126 to allow for movement of the needle 58 into and out of target tissue. In order to transmit this movement from the plunger carrier 138 to the cartridge carrier 126, one or more transfer instruments 150 are provided. As will be explained in greater detail below, the transfer instrument 150 may be moved selectively between a first position wherein the transfer instrument 150 engages only one of the either the cartridge carrier 126 or the plunger carrier 138, and a second position wherein the transfer instrument 150 engages both of the cartridge carrier 126 and the plunger carrier 138, in effect, connecting the cartridge carrier 126 and the plunger carrier 138 together for contemporaneous movement.

To provide this selective engagement, the transfer instrument 150 is moveably disposed within a channel 152 of the cartridge carrier 126 (see FIG. 9). The transfer instrument 150 is adapted to move laterally partially into detents or recesses 154, 156 in the plunger carrier 138 and guides 158 of the longitudinally extending rails 136 of the housing 52, respectively. In this way, when the transfer instrument 150 is disposed within the channel 152 of the cartridge carrier 126 and the recess 154 of the plunger carrier 138, the cartridge carrier 126 will be coupled to the plunger carrier 138 for movement with the plunger carrier 138 along the drive screw 114. Conversely, when the transfer instrument 150 is disposed within the channel 152 of the cartridge carrier 126 and the recess 156 of the guide 158, the cartridge carrier 126 will not travel with the plunger carrier 138; rather, in the illustrated embodiment, the cartridge carrier 126 will not move relative to the housing 52.

It will be appreciated by those of skill in the art that each of the recesses 154, 156 and the channel 152 could be described as openings. Further, it will be appreciated that, while the transfer instrument 150 is described herein as moving between a first position within the channel 152 of the cartridge carrier 126 and the recess 156 of the guide 158 to a second position within the recess 154 of the plunger carrier 138 and the channel 152 of the cartridge carrier 126, in an alternate embodiment, the transfer instrument 150 could disposed for movement between a first position within the recess 154 of the plunger carrier 138 to a second position within the recess 154 of the plunger carrier 138 and the channel 152 of the cartridge carrier 126.

Further, while the transfer instrument 150 may be described as being disposed or engaged in the channel 152 and one or the other of the recesses 154, 156, the transfer instrument 150 may be slightly larger than the combined the channel 152 and the one or the other of the recesses 154, 156. For the purposes of this disclosure and the appended claims, however, when the transfer instrument 150 is described as being disposed or engaged in one or the other of the recesses 154, 156 or in the first or second position, it will be understood that the terminology encompasses a structural relationship wherein the transfer instrument 150 is predominately disposed one way or the other such that the associated structures are substantially coupled together. That is, when the transfer instrument 150 is predominately disposed within the channel 152 and the recess 154, the plunger carrier 138 and the cartridge carrier 126 are coupled together; conversely, when the transfer instrument 150 is predominately disposed within channel 152 and the recess 156, the cartridge carrier 126 and the guide 158 are coupled together.

For clarity, FIGS. 10A-10E show components of the drive control mechanism 104, and their relative positions as they move during stages of actuation of the automatic injector 50. The illustrated embodiment includes two control transfer instruments, specifically two transfer instruments 150 that move through respective channels 152 in the cartridge carrier 126 between respective recesses 154, 156 in the plunger carrier 138 and the guides 158.

While the transfer instruments 150, channel 152, and recesses 154, 156 may be of any appropriate design, in the illustrated embodiment, the transfer instruments 150 have the shape of a cylinder, disc or puck, allowing it to move smoothly within the channel 152. Moreover, the transfer instruments 150 may be of any appropriate material. By way of example only, the transfer instruments 150 may be formed of a polymer, stainless steel, or a silicone or rubbery material.

The dimensions of the transfer instruments 150 are such that the transfer instrument is always removably engaged with at least two components of the drive control mechanism 104 simultaneously. In some stages of operation each transfer instrument 150 is removably engaged with the corresponding recess 156 of the guide 158 and channel 152 (visible in FIG. 9) of the cartridge carrier 126. In other stages of operation, each transfer instrument 150 is removably engaged with the channel 152 of the cartridge carrier 126 and the recess 154 of the plunger carrier 138. This novel configuration enables a single motor 106 and transmission assembly 110 to drive the function of multiple components, thereby simplifying the functionality of the automatic injector 50 and improving the reliability, operation, and manufacturing cost of the reusable automatic injector 50.

Likewise, the recesses 154, 156 of the plunger carrier 138 and the guides 158 can be a number of different configurations. In one embodiment of the present invention, the recesses 154, 156 of the plunger carrier 138 and the guides 158 are symmetrical within the respective components. The recesses 154, 156 have an arcuate shape that is ramped on either side to facilitate movement of the transfer instrument 150 as the transfer instrument 150 rides along the ramped surfaces. In this way, an at least partially rounded outer surface of the transfer instrument 150 may smoothly ride along the ramped surfaces.

Operation of the transfer instruments 150 and the respective movements of the cartridge carrier 126 and plunger carrier 138 may be better understood with respect to exemplary stages of operation of the automated injector 50. FIGS. 10A-10E and 11A-11B through 15A-B show the positioning of components of an embodiment of the automated injector 50 through the stages of cartridge 54 loading (FIGS. 10A and 11A-11B), removal of the rigid needle shield 60 (FIGS. 10B and 12A-12B), needle 58 injection (FIGS. 10C and 13A-13B), drug dose delivery (FIGS. 10D and 14A-14B), and needle retraction (FIGS. 10E and 15A-15B). FIGS. 11A, 12A, 13A, 14A, and 15A show the automatic injector 50 from a side view (cross-sectional lines having been eliminated in the interest of clarity), while FIGS. 11B, 12B, 13B, 14B, and 15B show automatic injector 50 from a top plan view. FIGS. 10A-10E show enlarged fragmentary top views of the operation of the transfer instruments 150 relative to the cartridge carrier 126, plunger carrier 138, and guides 158. For the sake of clarity, the plunger carrier 138 is broken away below the cradle 146, illustrating only the portion 144 of the plunger carrier 138 that rides between the rails 132 of the cartridge carrier 126.

A cartridge 54 is replaceably inserted into a cartridge carrier 126 of the reusable automatic injector 50 and held in place throughout the needle 58 injection and retraction process, as shown in FIGS. 11-15. The cartridge 54 may be held in place within the cartridge carrier 126 by, for example, one or more cartridge 54 connection features 130.

A cartridge sensor 160 positioned within the cartridge carrier 126 may optionally be utilized to sense when a cartridge 54 has been placed within the cartridge carrier 126 of reusable automatic injector 50. In the illustrated embodiment, the cartridge sensor 160 is disposed at the bottom of the housing 52, although it may be alternately positioned. Placement of the cartridge 54 within the cartridge carrier 126 such that the cartridge sensor 160 senses the presence of the cartridge 54 may provide an indication that permits the reusable automatic injector 50 to be activated.

The cartridge sensor 160 may be of any appropriate design. For example, the cartridge sensor 160 may be a mechanical sensor, such that placement of a cartridge 54 into the cartridge 54 carrier causes the displacement of the mechanical sensor. Alternatively, or additionally, the cartridge 54 sensor may be an electrical sensor.

Further, actuation of the cartridge sensor 160, whether electrical or mechanical, may be tied to operation of the automatic injector 50 such that actuation of the cartridge sensor 160, for example, allows the cartridge cover 72 to close and latch, or provides a signal to a processor allowing actuation of the automatic injector 50. Upon activation, the motor 106 may cause the transmission assembly 110 to drive the drive screw 114 into the correct position where the plunger interface feature 140 of the plunger carrier 138 is in contact with, or adjacent to, the proximal end of the plunger rod 66 of the cartridge 54.

In order to facilitate removal of the rigid needle shield 60, the automated injector 50 may include structure that engages the rigid needle shield 60 such that movement of the cartridge 54 in the proximal direction results in removal of the rigid needle shield 60. As may be seen in FIGS. 11A and 11B, the cartridge 54 may be positioned such that the rigid needle shield 60, which covers the needle 58 prior to injection for safety purposes, is removably locked into needle shield stripper features 162 of support housing 52. The needle shield stripper features 162 may be of any appropriate design. In the illustrated embodiment, for example, the needle shield stripper features 162 include one or more flanges 164 disposed along a proximally disposed edge of rigid needle shield 60. In this way, as the flanges 164 confront the rigid needle shield 60 during movement of the cartridge 54 in a proximal direction, the rigid needle shield 60 is disengaged from the distal end of the cartridge 54. Alternatively, the reusable automatic injector 50 may be configured such that the needle shield stripper features 162 of support housing 52 lock onto the barrel 56 between the barrel 56 and the rigid needle shield 60.

The function of the drive control mechanism, its components, and the automatic injector 50 may be better understood with reference to FIGS. 4, 6-8, and 10A-10E as they relate to FIGS. 11A-15B. In a first stage, typically for loading of a cartridge 54 into the automatic injector 50, the components of the drive control mechanism 104 are as shown in FIGS. 10A and 11A-11B. The guide 158 contains the recess 156, while the plunger carrier 138 similarly contains recess 154. As described herein, the guide 158 may be a separate component or a pre-formed aspect of the housing 52. Regardless of whether the guide(s) 158 are separate components or pre-formed aspects of the housing 52, they are considered as a part of the housing 52 for the purposes of this disclosure. The cartridge carrier 126 contains at least one channel 152. The drive control mechanism 104 may include a recess 156 within the guide 158, a recess 154 within the plunger carrier 138, and a channel 152 through the cartridge carrier 126 for each control transfer instrument 150 utilized by the automatic injector 50. For example, when two puck-shaped control transfer instruments are utilized in the automatic injector 50, as is shown in FIGS. 10A-10E, the drive control mechanism 104 includes two guide recesses 156, two plunger carrier recesses 154, and two channels 152 which are positioned and interact with the control transfer instruments 150, respectively. When the reusable automatic injector 50 is in the first stage for cartridge 54 loading, the components of the drive control mechanism 104 are aligned such that each transfer instrument 150 is allowed to freely pass between the guide recess 156, through the channel 152 of the cartridge carrier 126, and the plunger carrier recess 154, as illustrated in FIG. 10A.

To move the reusable automatic injector 50 into a second stage, generally considered the stage for removal of the rigid needle shield 60 from the needle 58, motor 106 and transmission assembly 110 cause the components of the drive control mechanism 104 to move in the proximal direction. This arrangement is shown in FIGS. 12A and 12B. While the rigid needle shield 60 is retained at the distal end of the reusable automatic injector 50, such as by interaction with the needle shield stripper features 162 of the support housing 52 for example, the components of the drive control mechanism 104 and the cartridge 54 are caused to move in the proximal direction. This action separates the rigid needle shield 60 from the needle 58. In an embodiment, the rigid needle shield 60 may be configured to "pop off" of the cartridge 54, such that the rigid needle shield 60 may be ejected from the reusable automatic injector 50, if desired. The cartridge 54 and the automatic injector 50 are now ready for injection into a patient.

FIG. 10B further details the interaction of the components of the drive control mechanism 104 as the automatic injector 50 moves from the loading stage (shown in FIGS. 11A and 11B) to the removal of the rigid needle shield 60 stage (shown in FIGS. 12A and 12B). While the guide 158, and accordingly the guide recesses 156, is a fixed position component, the cartridge carrier 126, plunger carrier 138, and drive screw 114 are all movable components. In the transition from the loading stage to the removal of the rigid needle shield 60 stage, the motor 106 and transmission assembly 110 cause the drive screw 114 to rotate such that the plunger carrier 138 is caused to move in the proximal direction, that is, from the respective positions illustrated in FIG. 10A to the respective positions illustrated in FIG. 10B. As the plunger carrier 138 moves rearward and the channel 152 of the cartridge carrier 126 becomes aligned with the recesses 154 of the plunger carrier 138, the transfer instruments 150 move inward, ensuring that the transfer instruments 150 are out of guide recesses 156 and into position between the channels 152 of the cartridge carrier 126 and the recesses 154 of the plunger carrier 138, as shown in FIG. 10B.

When the transfer instrument 150 is formed of a rubbery material and is slightly wider than the combined depth of the channel 152 and the guide recess 156, the transfer instrument 150 will protrude slightly into the recess 154 of the plunger carrier 138 when the recess 154 aligns with the recess 156 and the channel 152. As the plunger carrier 138 continues to move relative to the guide 158, the cartridge carrier 126 may move slightly with the plunger carrier 138 as a result of the force of the transfer instrument 150 acted upon by ramped surface of the recess 154 of the plunger carrier 138. The continued force of the ramped surface of the recess 154, the force of the ramped surface of the recess 156 in the opposite direction along an opposite side of the transfer instrument 150, creates a moment that causes the transfer instrument 150 to move from the recess 156 of the guide 158 into the recess 154 of the plunger carrier 138. With the placement of the transfer instrument 150 in the channel 152 of the cartridge carrier 126 and the recess 154 of the plunger carrier 138, the cartridge carrier 126 and plunger carrier 138 are coupled together for further movement.

This positioning of the transfer instruments 150 causes the cartridge carrier 126 and the plunger carrier 138 to move as one unified component. That is, as rotation of the drive screw 114 causes movement of the plunger carrier 138 in the proximal direction, the positioning of the control transfer instruments 150 with the recesses 154 of the plunger carrier 138 and the channels 152 of the cartridge carrier 126 couples the cartridge carrier 126 to the plunger carrier 138 so that the cartridge carrier 126 to also move in the proximal direction. In this way, motion of the plunger carrier 138 and the cartridge carrier 126 in the proximal direction moves the transfer instruments 150 away from the recesses 156 of the fixed position guide 158.

As stated above, one or more control transfer instruments 150 may be used in the drive control mechanisms and automatic injectors of the present invention. In at least one embodiment, however, two puck-shaped control transfer instruments are utilized to, for example, provide stronger connections, more even distribution of force on the components, and control the motion of the components.

Because the needle shield 60 of the cartridge 54 is removably confronted by the needle shield stripper features 162 of the housing 52 (shown in FIGS. 11A-11B), the rigid needle shield 60 is removed from the needle 58 by the proximal movement of the cartridge carrier 126 and the cartridge 54. This is shown in the transition between FIGS. 11A-11B and 12A and 12B, as well as the transition between FIGS. 10A and 10B. The reusable automatic injector 50 can now be placed in contact with target tissue of a patient to inject the needle 58 and deliver a drug contained within the cartridge 54.

Figure 13A:
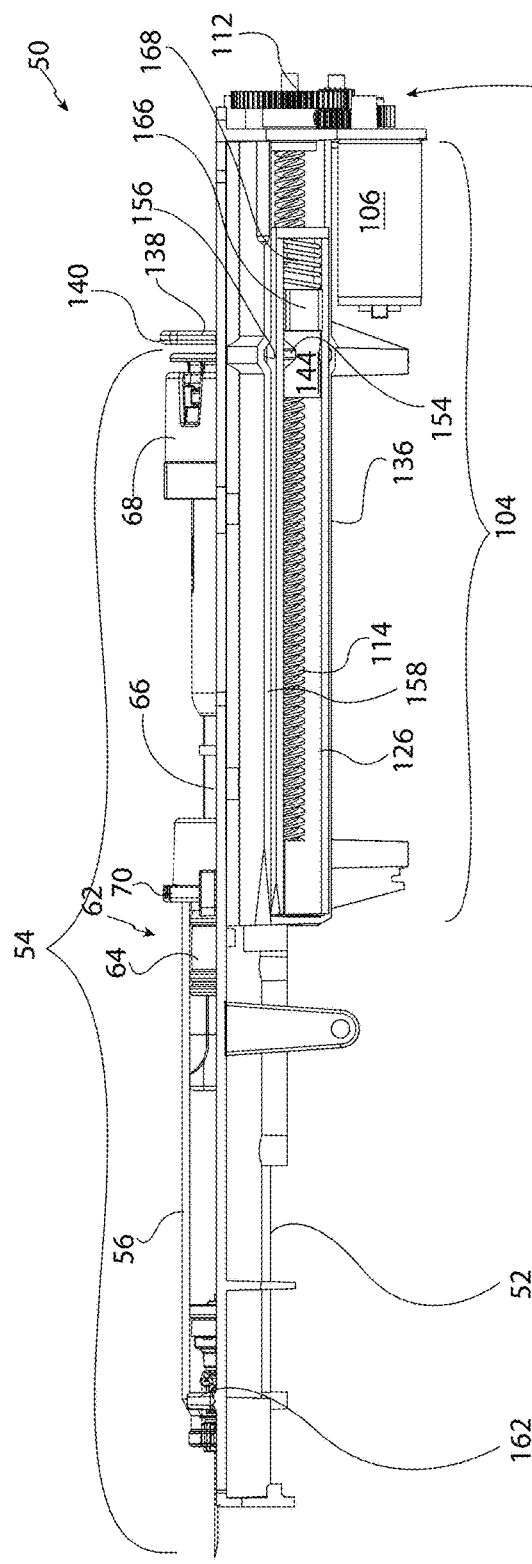
FIG. 13A is a side view of the reusable automatic injector, according to one embodiment of the present invention, shown in the injection configuration.
Figure 13B:
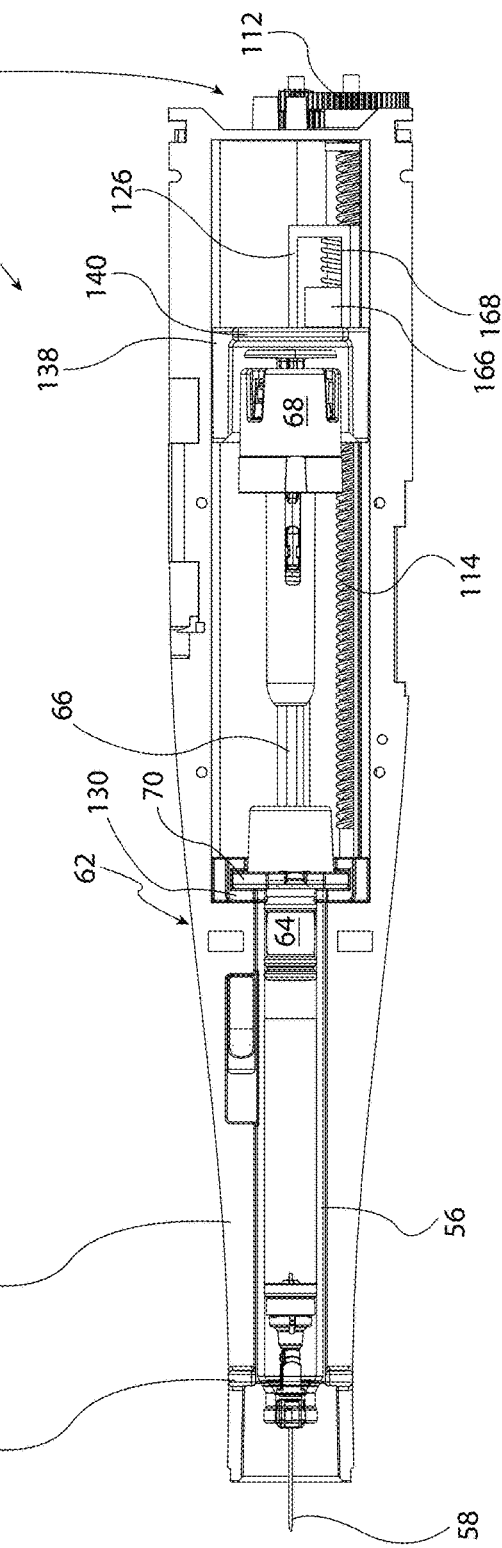
FIG. 13B is a top view of the reusable automatic injector shown in FIG. 13A.

Moving to FIGS. 13A-13B, during the injection stage, the cartridge carrier 126 and the plunger carrier 138 are caused to move in the distal direction, moving the now exposed needle 58 at the distal end of the reusable automatic injector 50 into an injection position in the target tissue of the patient. As described further herein, an optional patient sensor 165 (shown in FIGS. 1, 2 and 5) may be utilized to sense contact with the patient prior to operation of the injection stage. The patient sensor 165 may be positioned at the distal end of the reusable automatic injector 50, adjacent to and on the exterior side of the needle shield stripper feature 162 of the support housing 52. Upon contact with a patient, the patient sensor 165 may signal a control system that the patient is ready for injection, if one or more control systems are utilized to control the timing and parameters of motion. Alternatively, or additionally, the patient sensor 165 may be mechanically coupled to an arrangement that prevents administration of the drug from the cartridge 54 unless the patient sensor 165 is depressed.

As the cartridge carrier 126 and the plunger carrier 138 move in the distal direction, the components move from the position shown in FIG. 10B to the position shown in 10c. As shown in FIG. 10C, at the position wherein the needle 58 has been inserted into the target tissue, the channels 152 again align with the recesses 156 in the guides 158. As a result, the transfer instruments 150 are able to move freely between the plunger carrier recesses 154, the channels 152, and the guide recesses 156. The transfer instruments 150 may be in the "out" position (i.e., in the guide recesses 156) or in the "in" position (i.e., in the plunger carrier recesses 154). As the cartridge carrier 126 is moved into the furthest distal position as illustrated in FIGS. 13A and 13B, however, the plunger carrier 138 continues forward movement as a result of the rotation of the drive screw 114. With continued motion of the plunger carrier 138, the transfer instruments 150 ride along ramped edges of the recesses 154 of the plunger carrier 138, urging the transfer instruments 150 outward through the channels 152 in the stationary cartridge carrier 126 and toward the recesses 156 in the guides 158. In this way, the continued motion of the plunger carrier 138 causes the transfer instruments 150 to ride along the ramped sides of the recesses 154 of the plunger carrier 138 to move outward when the channels 152 of the cartridge carrier 126 are aligned with the recesses 156 of the guide 158, disengaging the transfer instruments 150 from the recesses 154 in the plunger carrier 138 to engage the transfer instruments 150 in the recesses 156 in the guide 158, that is, the position illustrated in FIG. 10D. In the position of FIG. 10D, the plunger carrier 138 is free to continue forward movement for drug delivery.

Depending on the desired injection parameters, the drug may be immediately delivered upon injection of the needle 58 or there may be a momentary delay between the two stages. Such parameters may be programmed into the control system or initiated by the user, as may be desired for operation of the reusable automatic injector 50.

For the drug delivery stage, the plunger carrier 138 may continue to move in the distal direction while the cartridge carrier 126 is temporarily locked into place with the guide 158, as illustrated in FIG. 10D. The locking occurs because the transfer instruments 150 are forced out of the plunger carrier recesses 154 and into position between the channels 152 of the cartridge carrier 126 and the guide recesses 156 of the guide 158. As the plunger carrier 138 continues to move in the distal direction, the plunger interface feature 140 of the plunger carrier 138 applies force to, or pushes upon, the distal end of the plunger rod 66. The plunger rod 66 relays that axial force in the distal direction to the plunger seal 64 within the barrel 56 of the cartridge 54, thereby forcing the drug fluid through the needle 58 and into the patient.

Through the drug delivery stage, as the components of the automatic injector 50 the transfer instruments 150 remains in the "out" position between the channels 152 and the guide recesses 156, as shown in FIG. 10d. It will be appreciated, however, that as the plunger carrier 138 moves to the position illustrated in FIGS. 14A and 14B, the portion 144 of the plunger carrier 138 disposed between the guides 158 moves beyond the position wherein the portion 144 causes an interference that would prevent the transfer instruments 150 from again traveling radially inward, that is, out of the recesses 156 in the guides 158 and the channels 152 in the cartridge carrier 126.

While any appropriate arrangement may be provided to retain the transfer instruments 150 in position, in the illustrated embodiment, a retainer 166 is provided. The retainer 166 may best be viewed in FIG. 4. By way of a retainer biasing element 168, such as the illustrated spring, the retainer 166 is disposed and biased toward a position that at least partially covers the channels 152 in the cartridge carrier 126 when the plunger carrier 138 is moved distally to deliver a drug from the cartridge 54. In this way, the retainer biasing element 168 and retainer 166 are configured to retain the transfer instruments 150 within the channels 152 and the guide recesses 156. For example, as shown in FIG. 10D, the retainer biasing element 168 is positioned at the proximal end of, and axially around, the drive screw 114 between the proximal end of the cartridge carrier 126 and the proximal end of the plunger carrier 138. The retainer biasing element 168 is initially in a compressed position, but is permitted to expand along the axis of the drive screw 114 when the plunger carrier 138 has moved distally. The retainer biasing element 168 acts upon the retainer 166 and moves the latter in the distal direction when the plunger carrier 138 has moved distally. As the plunger carrier 138 moves in the distal direction along the axis of the drive screw 114 during controlled drug delivery, the retainer 166, urged distally by the retainer biasing element 168, functions to keep the transfer instruments 150 within the drive control mechanism 104.

In order to provide controlled travel and function of the retainer 166 and retainer biasing element 168, the cartridge carrier 126 may include structure that guides and limits movement of the retainer 166. In the illustrated embodiment, a boss 170 including two arcuate segments 172 that extend between the rails 132 of the cartridge carrier 126 (see FIG. 9). The arcuate segments 172 are separated by longitudinally extending channels 174 that slidingly receive arms 176 extending from the retainer 166 (see FIG. 4). The arms 176 and/or the channels 174 may include structure, such as the enlarged ends 180 of the arms 176, that limit the movement of the retainer 166 in a distal direction. Those of skill will appreciate that the structures, such as the boss 170 may be formed unitarily with the cartridge carrier 126, for example, or may be formed as one or more separate components.

After the drug delivery stage has completed, as shown in FIGS. 14A-14B and FIG. 10D, the drive screw 114 may be caused to move in the proximal direction by the transmission assembly 110 and the motor 106, that is, for example, to the position illustrated in FIGS. 15A-15B and FIG. 10E. As the drive screw 114 causes motion in the proximal direction of the plunger carrier 138, such as by rotation of the drive screw 114 in the reverse or opposite direction from its earlier motion, the plunger carrier 138 engages the retainer 166 to return the retainer 166 its original position, again compressing the retainer biasing element 168 to the position shown in FIG. 10E. As the retainer 166 and plunger carrier 138 move in a proximal direction, along the axis of the drive screw 114, transfer instruments 150 are again permitted to move between the guide recesses 156 and channels 152 and into contact with the plunger recesses 154. Once this occurs, the cartridge carrier 126 is also caused to move in the proximal direction. Motion of the plunger carrier 138 and the cartridge carrier 126 in the proximal direction moves the transfer instruments 150 away from the guide recesses 156 of the fixed position guide 158. This motion causes the transfer instruments 150 to move radially inward as explained above, ensuring that the transfer instruments 150 disengage the guide recesses 156 and are positioned between the channels 152 of the cartridge carrier 126 and the recesses 154 of the plunger carrier 138. This positioning of the transfer instruments 150 causes the cartridge carrier 126 and the plunger carrier 138 to again move as one unified component. Movement of these unified components in the proximal direction causes the cartridge 54 to also move in the proximal direction.

If a safety syringe is utilized as a cartridge 54 of the automatic injector 50, safety mechanisms of the safety syringe may be triggered at the end of the drug delivery stage by operation of the syringe. Accordingly, the cartridge 54 disposed in the cartridge carrier 126 of the automatic injector 50 will be safe for removal and disposal by the user. Optionally, the user may reattach the rigid needle shield 60 to the distal end of the cartridge 54, such as to the distal end of the barrel 56, after the syringe has been used (i.e., drug delivery has completed). In the position illustrated in FIGS. 10e and 15a-15b, the automatic injector 50 is reset to its original configuration and again ready to accept another cartridge 54, thereby constituting a reusable automatic injector 50.

As discussed above, one or more sensors may be utilized for safety or for other reasons. For example, a patient sensor 165 may be utilized at a distal end of the reusable automatic injector 50 to ensure that it is in contact with the patient prior to needle injection. A cartridge sensor 160 may similarly be used to ensure that a cartridge 54 is correctly in position within the cartridge carrier 126 prior to operation. Other sensors known in the art may be utilized for this or other purposes and are contemplated and encompassed within the breadth of the embodiments of the present invention. Similarly, other components may optionally be utilized to enhance the safety and functionality of the automatic injector 50. For example, a cartridge ejector assembly 182 may be utilized to removably lock and eject the cartridge 54 during and after operation, respectively. One example of a cartridge ejector assembly 182 is shown in FIGS. 2 and 5.

Figure 16A:
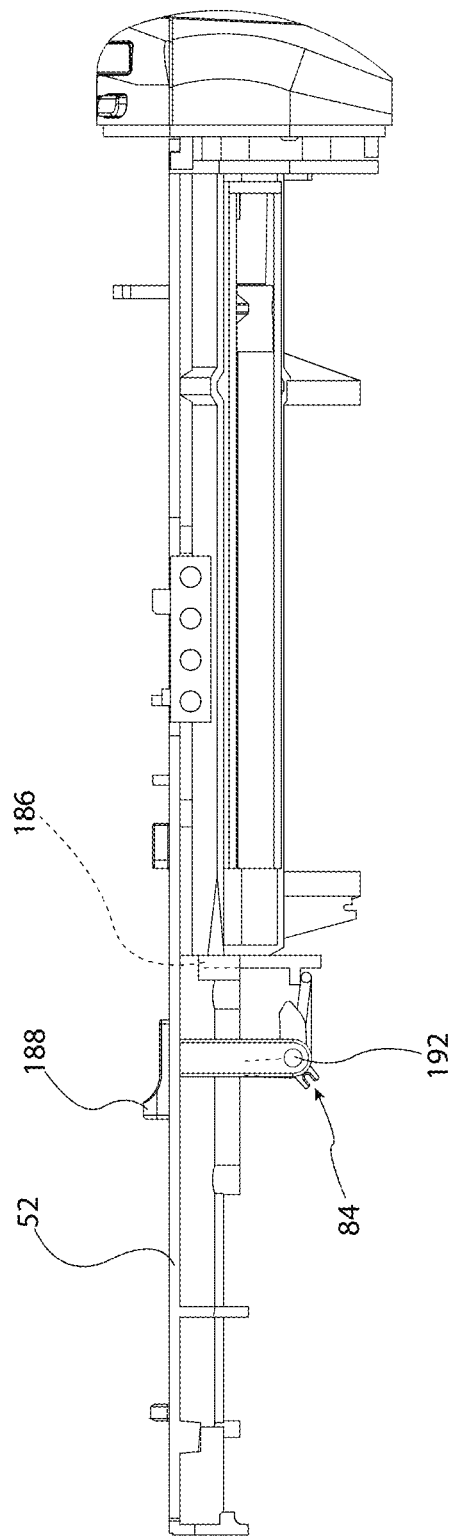
FIGS. 16A-16B are side elevational views of a housing including an embodiment of a cartridge ejector in the loaded and unloaded positions, respectively.
Figure 16B:
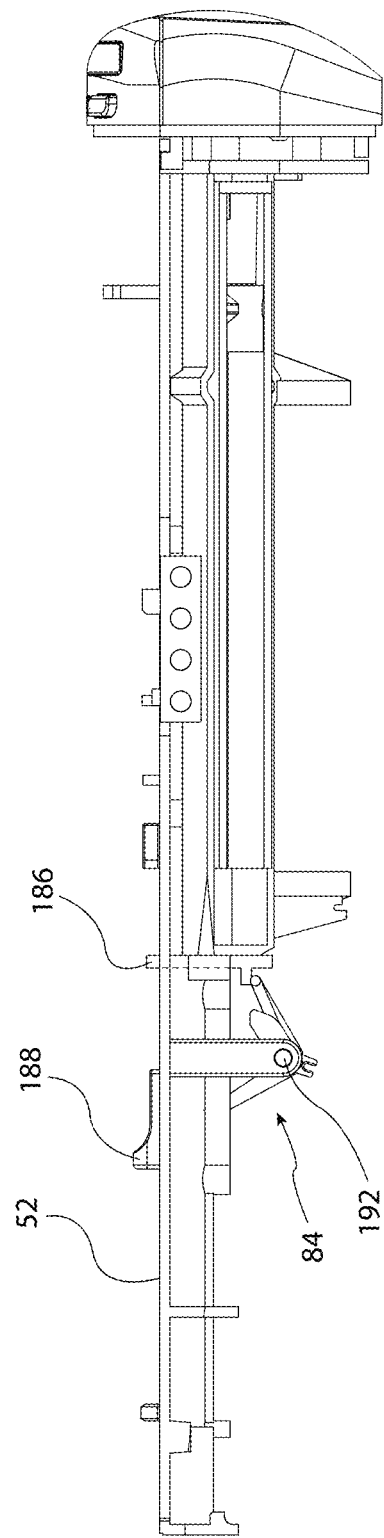

Another embodiment of a cartridge ejector assembly 184, which is shown in FIGS. 16A-16B, may alternately be provided to facilitate easy removal of the cartridge 54 from the housing 52. While the ejector assembly 184 may be of any appropriate design, in the illustrated embodiment, an ejector prong 186 is disposed to slide from a loaded position shown in FIG. 16A to the eject position shown in FIG. 16B as a result of movement of a toggle switch 188 disposed on the upper surface of the housing 52. When loading the cartridge 54 (not shown) into the housing 52, the toggle switch 188 may be manually moved to a position that disposes the ejector prong 186 below the level of a loaded cartridge 54, or the cartridge 54 may be utilized to depress the ejector prong 186 such that the ejector prong 186 is disposed subjacent the loaded cartridge 54, i.e., the position shown FIG. 16A. The ejector prong 186 of this embodiment is coupled to the toggle switch 188 by a linkage 190 that pivots about axis 192 to toggle the ejector prong 186 between the loaded position shown in FIG. 16A and the eject position shown in FIG. 16B. It will be appreciated, however, that any appropriate design may be utilized. For example, a cartridge ejector assembly may be configured to automatically eject a cartridge 54 upon completion of the drug dose delivery and retraction of the cartridge 54 or the needle 58 and the cartridge 54.

Figure 17:
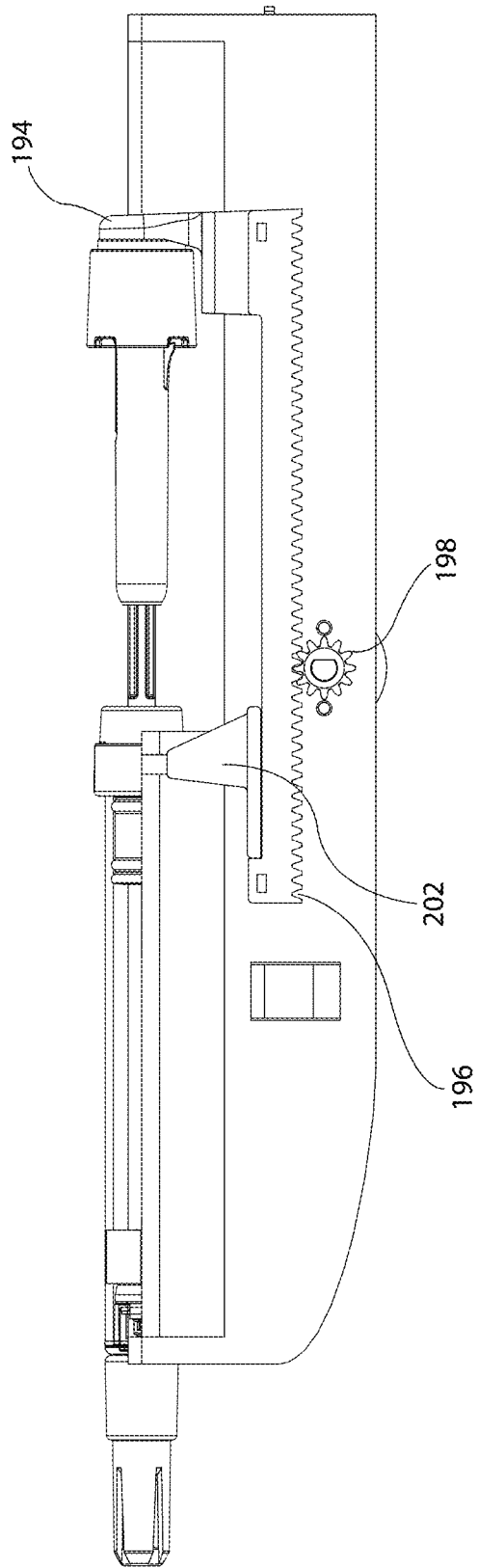
FIG. 17 is a side elevational view of an alternate embodiment of an automatic injector according to the invention.
Figure 18:
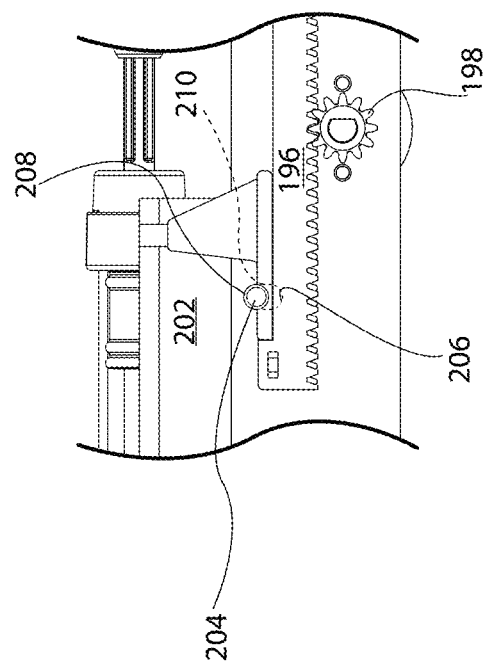
FIG. 18 is an enlarged, fragmentary view of components of the drive control mechanism of FIG. 17.

As mentioned above, there are various modifications which can be made within the contemplation of the embodiments of the present invention. For example, alternate gear trains and actuation arrangements may be provided. Referring to FIG. 17, in an alternate embodiment, longitudinal movement of a plunger carrier 194 may be provided by a gear train that includes a rack 196 and pinion gear 198 arrangement. In other words, the elongated drive device in this embodiment includes the rack 196, with is coupled to the plunger carrier 194. It will be appreciated that rotation of the pinion gear 198 engaged with the rack 196 causes the rack 196 and associated plunger carrier 194 to move between proximal and distal positions within a housing 200. The motion of the plunger carrier 194 may be selectively combined with motion of a cartridge carrier 202 by way of transfer instruments 204, illustrated, for example, in FIG. 18. The transfer instruments 204 shift between detents or recesses 206, 208 in the rack 196 and the cartridge carrier 202, respectively, through channels 210 in the cartridge carrier 202.

Figure 19:
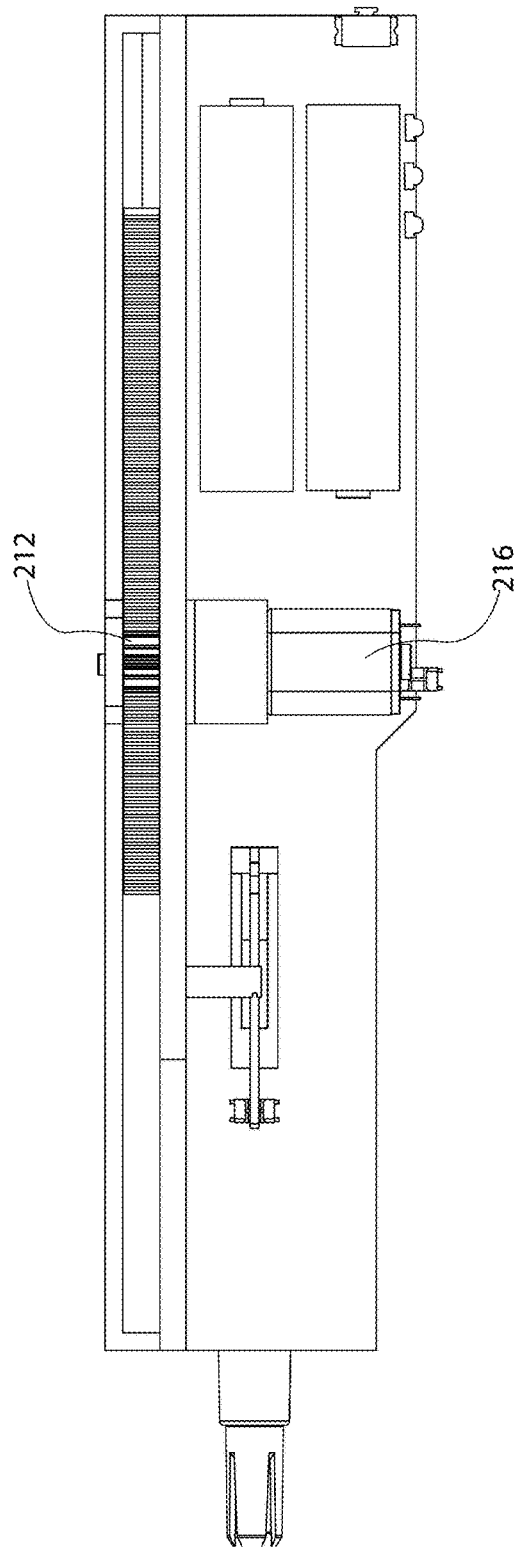
FIG. 19 is a bottom view of another embodiment of an automatic injector according to the invention.
Figure 20:
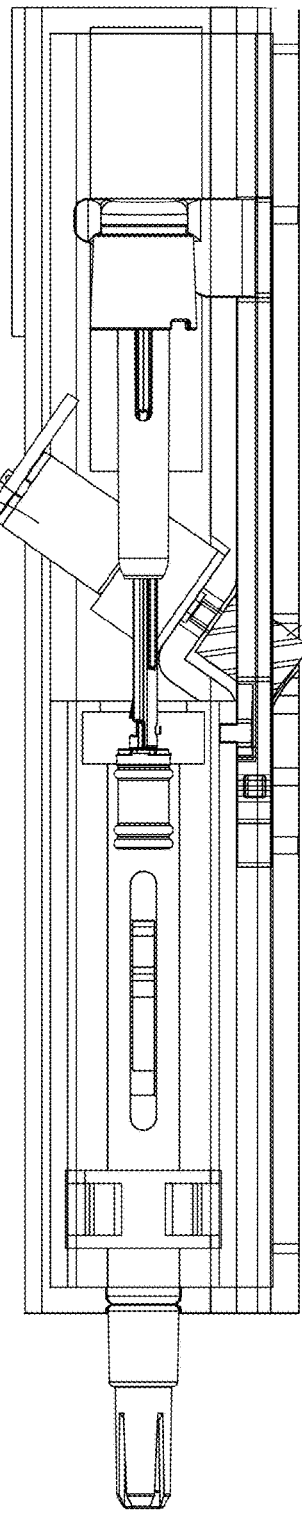
FIG. 20 is a top plan view of another embodiment of an automatic injector according to the invention.

In order to provide rotary motion to the pinion gear 212, 214, a motor 216, 218 may be disposed at an appropriate angle to provide direct rotation to the pinion gear 212, 214 as shown, for example, in FIGS. 19 and 20, respectively. Those of skill in the art will appreciate that the gear train may alternatively include additional gears that allow the motor to extend longitudinally within the automatic injector while still utilizing a rack in order to impart longitudinal motion to the plunger carrier (not illustrated).

Figure 21:
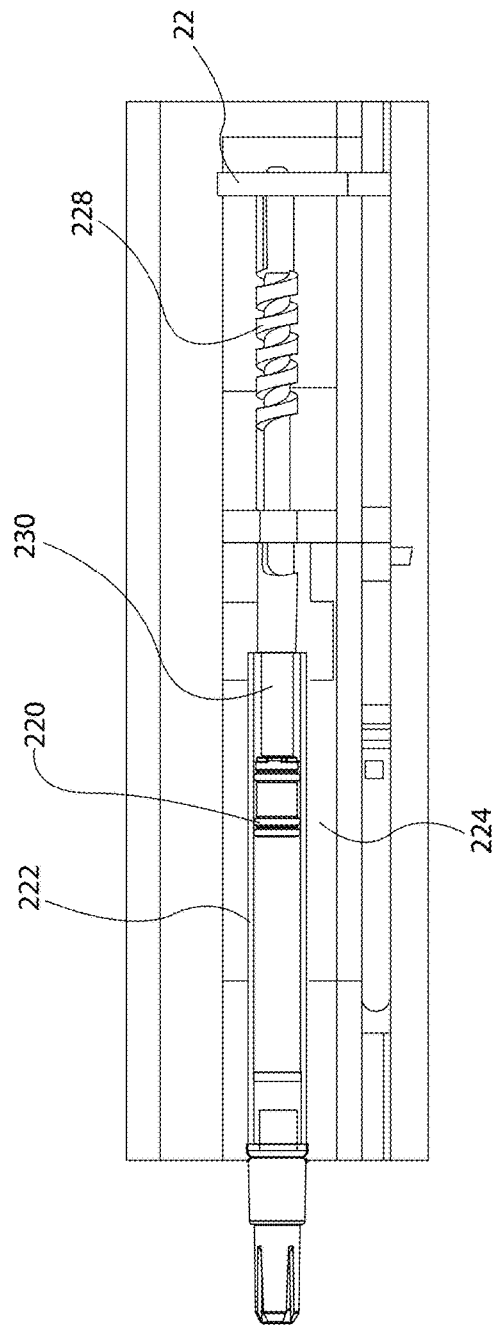
FIG. 21 is a top plan view of another embodiment of an automatic injector according to the invention.

The reusable automatic injectors described above utilize a standard syringe. However, the automatic injectors of the present invention, according to at least one other embodiment, may utilize a permanent plunger rod 228, such as is illustrated in FIG. 21, instead of a standard syringe plunger rod 66, such as is illustrated in FIGS. 11A through 15B. For example, the plunger interface feature 230 of plunger carrier 226, shown in FIG. 21, may include an elongated projection in the form of an elongated rod 228 which during operation would reside within the proximal end of the barrel 222 of cartridge 224 and with an interface feature 230 that acts directly upon a plunger seal 220. This configuration eliminates the need for the cartridge to include a plunger rod, thus enabling the use of various cartridges 224. In one such embodiment, after the cartridge 224 is inserted into the reusable automatic injector, the components of the drive control mechanism would cause the plunger interface feature 230 to directly engage the plunger seal 220 of the cartridge 224. Axial motion in the distal direction by the plunger carrier 226 and elongated rod 228 would cause the interface feature 230 to enter the proximal end of the barrel 222 of the cartridge 224. After this step, the function of the components of the drive control mechanism and the reusable automatic injector are as described above for the steps of: removal of rigid needle shield, needle injection, drug dose delivery, and needle retraction. In such embodiments, a final step may be performed after needle retraction to ensure that the cartridge 224 is removable from the elongated rod 228 and the plunger interface feature 230 and of the plunger carrier 226. Other similar configurations may be utilized for this function while remaining within the breadth and contemplation of the present invention.

Another such an embodiment is shown in FIGS. 23A-23B. In such embodiments, the syringe cartridge would consist of standard syringe components, but would not include a plunger rod. The reusable automatic injector 210 would include a permanent plunger rod 222 which would connect enter the proximal end of the syringe barrel 218 and connect with the plunger seal 220 during operation. The permanent plunger rod 222 is initially positioned between the plunger drive feature 230a and the proximal end of the syringe barrel 218, while passing through an aperture in a plunger nut 252. The permanent plunger rod 222 may have one or more portions which have a radial diameter smaller than the diameter of the aperture in the plunger nut to enable free axial motion through the plunger nut. The permanent plunger rod 222 may have another portion with a screw, having a pitch diameter and a groove diameter, wherein the pitch diameter of the screw is larger than the diameter of the aperture in the plunger nut. This causes the permanent plunger rod 222 to rotate axially as the screw portion comes in contact with the plunger nut 252.

In one such embodiment, after the syringe cartridge is inserted into the reusable automatic injector 210, the components of the drive control mechanism 26 would cause the plunger drive feature 230a to push upon permanent plunger rod 222. This axial motion in the distal direction of the permanent plunger rod 222 would cause the distal tip of the permanent plunger rod 222 to enter the proximal end of the syringe barrel. Once the permanent plunger rod 222 is translated axially in the distal direction to the point where the screw portion contacts the plunger nut 252, further axial translation in the distal direction of the permanent plunger rod 222 causes it to rotate axially. This axial rotation screws the distal tip of the permanent plunger rod 222 into the plunger seal 220 within the barrel 218, causing them to engage and move as a unified unit. After this step, the function of the components of the drive control mechanism and the reusable automatic injector 210 are as described above for the steps of: removal of rigid needle shield, needle injection, drug dose delivery, and needle retraction. In such embodiments, a final step may be performed after needle retraction to disconnect (or unscrew) the permanent plunger rod 222 from the plunger seal 220. Since the screw portion of the permanent plunger rod 222 is now distal to the plunger nut 252, movement of the permanent plunger rod 222 in the proximal direction will cause the permanent plunger rod 222 to axially rotate in the opposite direction and unscrew from the plunger seal 220. The movement of the permanent plunger rod 222 in the proximal direction may be caused by, for example, movement of the carriage drive and carriage in the proximal direction to retract the syringe). Other similar configurations may be utilized for this function while remaining within the breadth and contemplation of the present invention.

The automatic injector may also include a cover release safety mechanism that prevents the cartridge cover from opening during certain stages of operation. According to at least one embodiment of the present invention, a cartridge cover release safety mechanism can be operated by the drive control mechanism as it progresses through the stages of: syringe cartridge loading, removal of rigid needle shield, needle injection, drug dose delivery, and needle and/or cartridge retraction. In other words, the cover release safety mechanism permits opening of the cartridge cover only when the needle is not exposed to the user, i.e., during initial loading of the cartridge when the protective needle shield is in place and/or after drug delivery and optional retraction or shielding of the needle. The cover release safety mechanism prevents opening of the cartridge cover during other stages of operation, i.e., when the needle is exposed for drug delivery. In this way, the cover release safety mechanism operates to inhibit the user's inadvertent exposure to the needle to reduce or eliminate accidental needle stick injuries to the user, providing a highly desirable safety feature.

Figure 22A:
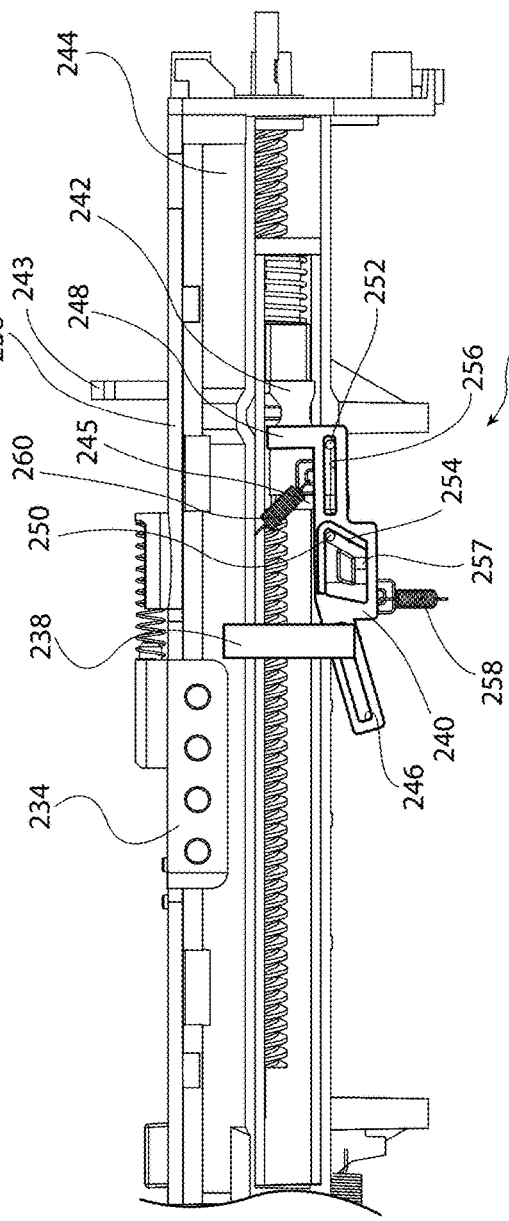

In the embodiment of FIGS. 22A-22E, for example, the cartridge cover release safety mechanism 232 is configured to be operated by the function of the drive control mechanism. The release actuator 234 is configured to slide in the proximal direction in order to release to cartridge cover (not shown) from the housing 236. The cartridge cover release safety mechanism 232 include a locking pin 238 that is adapted to move between an obstructing position that prevents movement of the release actuator 234 in a proximal direction (as shown in FIGS. 22B-22D), and a retracted position that allows movement of the release actuator 234 in a proximal direction (as shown in FIGS. 22A and 22E).

Movement of the locking pin 238 between the obstructing and retracted positions is at least partially controlled by a teeter 240. Movement of the teeter 240 is at least partially controlled by movement of the plunger carrier 242. In the illustrated views, and for the sake of simplicity, only the portion of the plunger carrier 242 disposed between the guides 244 and the plunger interaction feature 243 are illustrated. In this embodiment, the plunger carrier includes a downwardly depending flange 245. The teeter 240 includes a channel 246 that receives an aspect at the lower end of the locking pin 238 and a catch arm 248 that is disposed to engage the flange 245 of the plunger carrier 242.

In order to control movement of the teeter 240, a guide pin 250 and a fulcrum pin 252, both of which are fixed protrusions from the housing 236. The teeter 240 includes a pair of channels 254, 256 disposed receive the guide pin 250 and fulcrum pin 252, respectfully, to control movement of the teeter 240 as it slides in a plane. The teeter 240 adapted to move along a predetermine path as the guide channel 254 travels over the guide pin 250, movement of the slide channel 256 relative to the fulcrum pin 252 allowing the teeter 240 to slide and pivot for angular changes of the teeter 240 relative to the fulcrum pin 252. As the guide pin 250 travels within the guide channel 254 during the operation of the cartridge cover release safety mechanism 232, the guide pin 250 may be caused to removably rest within guide pin recess 257 of the guide channel 254. Biasing elements 258, 260, such as springs coupled to the housing 236 (for the sake of simplicity, specific sections of the housing 236 to which the springs are coupled are not illustrated), may be utilized to direct the positioning of the cartridge cover release safety mechanism 232, specifically, the teeter 240, during operation.

FIG. 22A shows the locking pin 238 of the cartridge cover release safety mechanism 232 in the initial retracted position, which allows the latch release to be manipulated (e.g., slid axially) to open the cartridge cover for loading of the cartridge into the automatic injector. In this position, the flange 245 of the plunger carrier 242 is not in contact with the corresponding catch arm 248 of the teeter 240 of the cartridge cover release safety mechanism 232.

As the syringe cartridge is loaded into the automatic injector, and the automatic injector is activated by the user, the flange 245 of the plunger carrier 242 is caused to translate axially in the proximal direction to retract the cartridge for removal of a rigid needle protector, for example. As the plunger carrier 242 moves proximally, the flange 245 comes into contact with the corresponding catch arm 248 of the teeter 240 of the cartridge cover release safety mechanism 232, thereby pulling the catch arm 248 of the teeter 240 in the proximal direction (see FIG. 22B). As the teeter 240 is pulled proximally, the guide channel 254 shifts upon guide pin 250 and the slide channel 256 slides and pivots along the fulcrum pin 252. Guide pin 250 is caused to removably move into position within guide pin recess 257, which causes the locking pin 238 to shift upwards into the obstructing position next to latch release. This prevents latch release from being moved to unlock and open the cartridge cover. The teeter 240 and locking pin 238 are retained in this position while the drive mechanism moves the plunger carrier 242 to perform the steps of drug delivery, including needle insertion and drug dosing to the user, as shown in FIG. 22C and FIG. 22*d*, respectively.

As shown in FIG. 22*e*, upon completion of drug dose delivery and, optionally, needle and/or cartridge retraction, the plunger carrier 242 is caused to translate axially in the proximal direction again. The plunger carrier 242 again comes into contact with the corresponding catch arm 248 of the teeter 240 of the cartridge cover release safety mechanism 232, thereby pulling catch arm 248 of the teeter 240 in the proximal direction. This motion, along with the biasing force of the biasing elements 258, 260 causes guide pin 250 to move from the guide pin recess 257 of the guide channel 254 of the teeter 240, and slide along the guide channel 254 to a final position where the angle of the teeter 240 pulls locking pin 238 out of the obstructing position with latch release. At this time, the release actuator 234 may again be freely operated to open the cartridge cover (e.g., to remove the used syringe cartridge). In this way, by blocking the release actuator 234 and maintaining the cartridge cover in a closed and locked position during operation of the reusable automatic injector, the user is typically prevented from exposure to the cartridge until the cartridge has been returned to a safe (e.g., retracted, shielded, sheathed) position for the user.

As previously stated, the transfer instrument may be sized and shaped in a number of different ways while maintaining its novel functional aspects. In at least one embodiment, the transfer instrument may be a cylinder which functions to connect the components of the drive control mechanism and facilitate the movement of the components through the various stages described above. Also as described above, certain components may be individual components or multiple components which work together. These components may be separate parts which function together, for ease of manufacturing for example, or be a single part that provides more than one function. The shapes and configurations described herein are also merely exemplary and other similar shapes having the same functionality may be utilized, within the breadth and contemplation of the present invention.

In a further embodiment of the present invention, a drive control mechanism for a reusable automatic injector 50 includes a drive screw 114, a cartridge carrier 126, a plunger carrier 138, and two transfer instruments 150. The drive control mechanism may further include, for each transfer instrument, a plunger carrier recess 154 on the plunger carrier 138, a channel 152 within the cartridge carrier 126 28, and a guide recess 156 on the guide 158. These components are sized and configured such that the control transfer instruments are retained within the drive control mechanism and the guide. For example, the cartridge carrier 126 may be a thin object having a rectangular bore through it as a channel. The transfer instrument may reside within the channel, but would be prevented from moving laterally along the axial plane of the cartridge carrier 126 because it is retained on all four sides. The dimensions of the transfer instrument 150 are such that the transfer instrument is always removably engaged with two components of the drive control mechanism 104 simultaneously. For example, in some stages of operation the transfer instrument 150 is removably engaged with the guide recess 156 of the guide 158 and the channel 152 of the cartridge carrier 126. In other stages of operation, the transfer instrument 150 is removably engaged with the channel 152 of the cartridge carrier 126 and the plunger carrier recess 154 of the plunger carrier 138. The drive control mechanism functions by forcing the transfer instrument between the plunger carrier recess 154 of the plunger carrier 138, the channel 152 within the cartridge carrier 126, and the guide recess 156 of the guide 158, such that a single motor 106 and transmission assembly 110 acting upon a drive screw 114 can control the function of the multiple components, as described above.

The reusable automatic injectors of the present invention are able to accommodate partially or fully filled cartridges 54, 224 of varying capacity, including 1 mL cartridges 54, 224. The reusable automatic injector could be used with retractable or safety syringes, including prefilled syringes, as well as with non-safety syringes. When used with a non-safety syringe, the cartridge 54, 224 is fully withdrawn back into the reusable automatic injector housing 52 after the injection to protect the user from exposed needles 58. Following the injection complete signal, the user can re-cap the non-safety syringe whilst it remains in the reusable automatic injector housing 52 with no risk of a needle 58 stick injury as the needle 58 point is contained inside the housing 52. The reusable automatic injector or cartridge cover 72 can then be opened and the used cartridge 54, 224 can be safely disposed in a sharps container. The reusable automatic injector would therefore provide a safe injection for non-safety syringes in addition to working with most retractable needle syringes. The present invention also provides reusable auto-injectors which are ergonomic, easy-to-use and aesthetically similar to products currently employed by self-administering patients. The automatic injectors of the present invention provide sufficient force at suitable speeds to simulate an injection by a nurse or doctor, yet provide the freedom of use for self-administering patients. The reusable automatic injectors of the present invention are also configured to withstand frequent use, such as daily use, over an extended period of time. The energy source which powers the reusable automatic injectors may similarly be replaceable, rechargeable, or otherwise provide power for use of the injectors over an extended period of time. The present invention thereby provides a reusable automatic injector with integrated safety mechanisms, enabled by incorporating a retractable needle syringe within the reusable automatic injector, in a convenient and easy-to-use package for patients.

One or more of the embodiments described above may provide additional desirable features to the patient. For example, the novel automatic injectors of the present invention may utilize existing or additional components within the housing to limit the depth of needle insertion. In one such embodiment, features located on the housing or the guide may be utilized for this purpose. In another embodiment, mechanical limits may be integrated into the drive control mechanism, the cartridge carrier, the plunger carrier, or the drive screw to limit the range of travel of the syringe needle into the patient. Similarly, as described above, one or more components may be employed to automatically remove the needle shield from the syringe needle upon activation of the reusable auto-injector.

In another embodiment, a single automatic injector according to the invention may be adjusted to accommodate cartridges including needles of various lengths. In this way, a single automatic injector may be utilized, for example, for intramuscular injections and subcutaneous injections. In adjusting for various needle lengths, the automatic injector may include a mechanical adjustment and/or an electrical adjustment, for example, by way of the user interface. The depth of needle insertion may be adjusted based upon the movement of the cartridge carrier within the housing, that is, as the cartridge and needle are moved to the position illustrated in FIGS. 13A and 13B.

According to another aspect of the invention, the processor of some embodiments may be programmed to precisely control the dose of medication administered. For example, when a cartridge includes a larger volume than required for administration, the automatic injector may be directed to dispense the unneeded volume prior to placement on the target tissue. The user interface may be utilized to program the automatic injector to dispense the unneeded volume prior to administration, for example, so long as the patient sensor 165 is not depressed. Accordingly, the automatic injector may be configured to expend a portion of the drug dosage to a reservoir or to the environment, prior to needle injection and drug dose delivery into a user, in order to reduce or adjust drug volume. The automatic injector may then be placed against the target tissue, actuating the patient sensor 165 to allow for dose administration. In another embodiment, the automatic injector may be programmed to insert the needle, administer the programmed volume of medication, and then move the cartridge in the proximal direction to retract the needle from the target tissue.

In further embodiments, the automatic injector may include one or more overrides. For example, the automatic injector may include an electronic override that may be actuated by way of the user interface. Alternatively or additionally, the automatic injector may include a manual override. For example, removal of the automatic injector from the target tissue such that the patient sensor 165 is no longer activated may cause the plunger carrier to cease progression and the cartridge carrier to retract the needle into the housing.

In another embodiment, the present invention relates to the method for manufacturing automatic injectors. The method includes the steps of assembling a drive control mechanism which includes an elongated drive device, such as a drive screw 114 or a rack 196, a cartridge carrier 126, a plunger carrier 138, and one or more control transfer instruments 150. The drive control mechanism may further include one or more plunger carrier recess(es) 154 within the plunger carrier 138, channels 152 within the cartridge carrier 126, and guide recess(es) 156 of the guide 158. These components are sized and configured such that the control transfer instruments 150 (e.g., pucks) are retained within the drive control mechanism and the guide. The method further includes the step of attaching a guide and a support housing 52 to the drive control mechanism. The method may further include the steps of attaching one or more of: an energy source, a motor 106, a transmission assembly 110, a control system such as a microprocessor, wherein the transmission assembly 110 is made to contact the drive screw 114. A cartridge 54 or housing 52 cover 72 may also be attached on the top side of the automatic injector.

In yet another embodiment, the present invention relates to a method of use for an automatic injector. The method includes the steps of: inserting a cartridge 54 into the carriage contained in a housing 52 of the automatic injector and activating the automatic injector to initiate, optionally, one or more of: removal of a needle shield 60, injection of a needle 58 into a patient, delivery of drug through the needle 58 to the patient, retraction of the needle 58 from the patient into the housing 52, and removal of the cartridge 54 from the cartridge carrier 126. Furthermore, optionally, the method of use may include the step of expending a portion of the drug dosage to a reservoir or to the environment, prior to needle injection and drug dose delivery into a user, in order to reduce or adjust drug dose volume. Similarly, optionally, the method of use may include the step of adjusting the range of axial translation of the drive mechanism (and therefore the syringe cartridge) to accommodate different needle lengths and/or injection depths. The method may further include the steps of opening a cartridge cover 72 to access an interior of the automatic injector prior to the insertion of a cartridge 54 into the cartridge carrier 126, and the step of closing the cartridge cover 72 after the cartridge 54 has been loaded into the cartridge carrier 126. The method may similarly include the step of opening the cartridge 54 or housing 52 cover 72 to access an interior of the automatic injector after the retraction of the needle 58 to remove the used cartridge 54. The user may optionally reattach the needle shield 60 to the cartridge 54 prior to removal of the cartridge 54 from the cartridge carrier 126. After the used cartridge 54 has been removed from the cartridge carrier 126 of the automatic injector, the automatic injector is reset and ready to accept another cartridge 54.

The embodiments shown and detailed herein disclose only a few possible variations of the present invention; other similar variations are contemplated and incorporated within the breadth of this disclosure. As would be readily appreciated by an ordinarily skilled artisan, a number of parameters, shapes, and dimensions described above may be modified while remaining within the breadth and scope of the present invention. For example, the distance that the cartridge carrier 126 moves in the distal direction may be adjusted to ensure that a predetermined depth of needle 58 insertion is met. Additionally or alternatively, other standard components such as stop members to prevent the travel of the carrier may be utilized to achieve this or similar functions. Other features may similarly be adjustable. For example, the automatic injector may be configured to accept different gear ratios and drive screw or rack pitches to provide desired injection speeds for a range of drug viscosities and patient requirements. The present invention provides drive control mechanisms, reusable automatic injectors, methods of manufacturing such automatic injectors, and their methods of use. As stated above, the drive control mechanisms and reusable automatic injectors may be utilized in a number of different configurations and may themselves comprise of one or more components. Other components may similarly be single components, unified components, or multi-purpose components, as described in the embodiments discussed above. Such novel automatic injectors may be employed by, for example, patients who are required to self-inject their medication on a regular or long-term basis. Accordingly, similar to the examples provided above, the novel reusable auto-injectors of the present invention may be configured, modified, and utilized to initiate drug delivery and activate needle retraction in any number of configurations while remaining within the breadth and scope of the present invention. Thus, it is intended that the present invention covers the modifications and variations of this invention provided they come within the scope of the appended claims and their equivalents.

The incorporation of the syringe retraction or the integrated needle retraction syringe into a reusable auto-injector enables patients to safely self-administer pharmaceutical treatment in an easy-to-use manner. The incorporation of the novel safety syringe features and designs into the reusable automatic injector provides a true end of dose indicator. Additionally, a standard syringe may be utilized and retracted into the body of the automatic injector to provide needle safety and to indicate that the dose is complete. While the syringes described herein may have integrated safety features, the automatic injectors of the present invention may be utilized with conventional syringes that lack such features.

The incorporation of such syringes into a disposable or reusable automatic injector extends the integrated safety mechanisms of the syringes into an automated drug delivery device that is highly desirable by patients. More specifically, automatic injectors that employ the integrated needle retraction safety syringes described herein may utilize the prefilled syringe's retraction mechanism instead of, or in addition too, other retraction mechanisms of the automatic injector such as the reverse drive mechanisms. Additionally, such automatic injectors also solve a significant unmet need is for an automatic injector with a true end of dose indicator. Currently visual, tactile or audible indicators are generally linked to the end of stroke or some other mechanical mechanism and not to the end of dose. The integrated needle retraction safety syringe retracts the needle into the syringe barrel, removing it from the patient's skin, once the dose is complete. Therefore, incorporating such integrated safety syringes into an automatic injector incorporates this true end of dose indicator. The embodiments of the present invention provide drive mechanisms, automatic injector configurations, and methods for manufacturing and using reusable automatic injectors. Such novel devices may be employed by, for example, patients who are required to self-inject their medication on a regular or long-term basis.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

We claim:

1. A method of operating an automatic injector to inject a fluid from a cartridge, the method comprising:
   disposing the cartridge in the automatic injector with at least a portion of a barrel disposed within a cartridge carrier, and a plunger assembly disposed for confrontation with a plunger carrier, a needle end of the cartridge defining a distal end of the automatic injector and an opposite end of the cartridge defining a proximal end of the automatic injector;
   coupling the cartridge carrier to the plunger carrier, the coupling including moving at least one transfer instrument from a first position, in which the transfer instrument engages only one of the either the cartridge carrier or the plunger carrier, to a second position, in which the transfer instrument engages both the cartridge carrier and the plunger carrier to couple the cartridge carrier and the plunger carrier together for contemporaneous movement;
   utilizing a single drive mechanism to move the plunger carrier and the cartridge carrier to advance the cartridge in an axial direction toward the distal end;
   decoupling the cartridge carrier from the plunger carrier;
   utilizing the drive mechanism to move the plunger carrier in the axial direction toward the distal end to dispense the fluid; and
   retracting the plunger carrier in an axial direction toward the proximal end.

2. The method of claim 1 further including actuating the automatic injector.

3. The method of claim 1 further including covering the cartridge with a cartridge cover.

4. The method of claim 1 further including removably coupling the cartridge carrier to the plunger carrier and utilizing the drive mechanism to move the cartridge carrier and the plunger carrier in the axial direction toward the proximal end following dispensing of the fluid.

5. The method of claim 1 further including utilizing the single drive mechanism to move the removably coupled cartridge carrier and plunger carrier in the axial direction toward the proximal end to disengage a needle shield from the cartridge prior to moving the plunger carrier and cartridge carrier in the axial direction toward the distal end.

6. The method of claim 1 wherein utilizing a single drive mechanism to move the plunger carrier and the cartridge carrier includes imparting movement to an elongated drive device coupled to the plunger carrier.

7. The method of claim 6 including operating a motor to impart movement to the elongated drive device.

8. The method of claim 7 wherein the step of operating the motor includes coupling an output of the motor to the elongated drive device with at least one gear.

9. The method of claim 1 wherein decoupling the cartridge carrier from the plunger carrier includes moving the at least one transfer instrument from the second position to the first position.

10. The method of claim 1 wherein the transfer instrument engages an opening in only one of the either the cartridge carrier or the plunger carrier in the first position, and wherein the transfer instrument engages openings in both of the cartridge carrier and the plunger carrier, in the second position.

11. The method of claim 1 wherein wherein the transfer instrument engages an opening in the cartridge carrier and an opening in a housing in the first position and wherein the transfer instrument engages the opening in the cartridge carrier and an opening in the plunger carrier in the second position.

12. The method of claim 1 wherein utilizing a single drive mechanism includes imparting movement to a threaded drive screw and drivingly engaging at least portion of the threads of the threaded drive screw with threads of the plunger assembly.

13. The method of claim 1 further including actuating an ejector to eject the cartridge following retraction.

14. The method of claim 1 further including operating a user interface.

15. The method of claim 1, further comprising:
    removing the cartridge from the housing;
    disposing a second cartridge in the housing; and
    actuating the automatic injector to dispense fluid from the second cartridge.

16. A method of operating an automatic injector to inject a fluid from a cartridge, the method comprising:
    disposing the cartridge in the automatic injector with at least a portion of a barrel disposed within a cartridge carrier, and a plunger assembly disposed for confrontation with a plunger carrier, a needle end of the cartridge defining a distal end of the automatic injector and an opposite end of the cartridge defining a proximal end of the automatic injector;
removably coupling the cartridge carrier to the plunger carrier;
utilizing a single drive mechanism to move the plunger carrier and the cartridge carrier to advance the cartridge in an axial direction toward the distal end;
decoupling the cartridge carrier from the plunger carrier;
utilizing the drive mechanism to move the plunger carrier in the axial direction toward the distal end to dispense the fluid;
recoupling the cartridge carrier to the plunger carrier; and
utilizing the drive mechanism to move the cartridge carrier and the plunger carrier in the axial toward the proximal end following dispensing of the fluid.

17. A method of operating an automatic injector to inject a fluid from a cartridge, the method comprising:
disposing the cartridge in the automatic injector with at least a portion of a barrel disposed within a cartridge carrier, and a plunger assembly disposed for confrontation with a plunger carrier, a needle end of the cartridge defining a distal end of the automatic injector and an opposite end of the cartridge defining a proximal end of the automatic injector;
coupling the cartridge carrier to the plunger carrier;
utilizing a single drive mechanism to move the plunger carrier and the cartridge carrier to advance the cartridge in an axial direction toward the distal end, the utilizing the single drive mechanism including imparting movement to a threaded drive screw and drivingly engaging at least portion of threads of the threaded drive screw with threads of the plunger assembly;
decoupling the cartridge carrier from the plunger carrier;
utilizing the drive mechanism to move the plunger carrier in the axial direction toward the distal end to dispense the fluid; and
retracting the plunger carrier in an axial direction toward the proximal end.

* * * * *

UNITED STATES PATENT AND TRADEMARK OFFICE
CERTIFICATE OF CORRECTION

PATENT NO. : 10,894,128 B2
APPLICATION NO. : 16/031419
DATED : January 19, 2021
INVENTOR(S) : Kevin Bokelman et al.

Page 1 of 1

It is certified that error appears in the above-identified patent and that said Letters Patent is hereby corrected as shown below:

In the Claims

In Claim 11, Column 30, Line 41, please delete "wherein".

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*